US009597419B2

(12) United States Patent
Fritz et al.

(10) Patent No.: US 9,597,419 B2
(45) Date of Patent: *Mar. 21, 2017

(54) LOADABLE POLYMERIC PARTICLES FOR ENHANCED IMAGING IN CLINICAL APPLICATIONS AND METHODS OF PREPARING AND USING THE SAME

(71) Applicants: Boston Scientific Limited, Maple Grove, MN (US); Gretchen B. Wojcik, Woodstock, GA (US)

(72) Inventors: Ulf Fritz, Hirschhorn (DE); Olaf Fritz, Hirschhorn (DE); Thomas A. Gordy, Newnan, GA (US); Ronald Wojcik, Canton, GA (US); Jacques Blümmel, Mannheim (DE); Alexander Küller, Hiedelberg (DE)

(73) Assignee: Boston Scientific Limited, Hamilton (BM)

( * ) Notice: Subject to any disclaimer, the term of this patent is extended or adjusted under 35 U.S.C. 154(b) by 0 days.

This patent is subject to a terminal disclaimer.

(21) Appl. No.: 14/693,190

(22) Filed: Apr. 22, 2015

(65) Prior Publication Data
US 2015/0258224 A1   Sep. 17, 2015

Related U.S. Application Data

(60) Division of application No. 11/877,839, filed on Oct. 24, 2007, now Pat. No. 9,114,162, which is a continuation-in-part of application No. 11/257,535, filed on Oct. 25, 2005, now Pat. No. 8,318,209.

(60) Provisional application No. 60/684,307, filed on May 24, 2005, provisional application No. 60/621,729, filed on Oct. 25, 2004.

(51) Int. Cl.
*A61K 49/04* (2006.01)
*A61K 51/12* (2006.01)
*A61K 49/18* (2006.01)
*A61K 49/22* (2006.01)

(52) U.S. Cl.
CPC ...... *A61K 51/1244* (2013.01); *A61K 49/0419* (2013.01); *A61K 49/1824* (2013.01); *A61K 49/225* (2013.01)

(58) Field of Classification Search
None
See application file for complete search history.

(56) References Cited

U.S. PATENT DOCUMENTS

| 3,949,073 | A | 4/1976 | Daniels et al. |
|---|---|---|---|
| 4,107,288 | A | 8/1978 | Oppenheim et al. |
| 4,124,705 | A | 11/1978 | Rothman et al. |
| 4,166,800 | A | 9/1979 | Fong |
| 4,311,736 | A | 1/1982 | Leong |
| 4,318,947 | A | 3/1982 | Joung |
| 4,341,844 | A | 7/1982 | Leong |
| 4,373,217 | A | 2/1983 | Draenert |
| 4,424,208 | A | 1/1984 | Wallace et al. |
| 4,424,395 | A | 1/1984 | Strom |
| 4,440,750 | A | 4/1984 | Glowacki et al. |
| 4,451,647 | A | 5/1984 | Allcock et al. |
| 4,452,916 | A | 6/1984 | Boschetti |
| 4,480,642 | A | 11/1984 | Stoy et al. |
| 4,507,123 | A | 3/1985 | Yoshida |
| 4,535,485 | A | 8/1985 | Ashman et al. |
| 4,537,916 | A | 8/1985 | Bruschtein et al. |
| 4,547,390 | A | 10/1985 | Ashman et al. |
| 4,557,764 | A | 12/1985 | Chu |
| 4,565,580 | A | 1/1986 | Miyata et al. |
| 4,579,880 | A | 4/1986 | Ohashi |
| 4,582,640 | A | 4/1986 | Smestad et al. |
| 4,592,755 | A | 6/1986 | Penton et al. |
| 4,595,713 | A | 6/1986 | St. John |
| 4,677,173 | A | 6/1987 | Holle et al. |
| 4,698,373 | A | 10/1987 | Tateosian et al. |

(Continued)

FOREIGN PATENT DOCUMENTS

| CA | 1252253 | 4/1989 |
|---|---|---|
| DE | 19613048 C2 | 10/1996 |

(Continued)

OTHER PUBLICATIONS

Steely, Lee Brent, "Hydrophobic and Hydrophilic Control in Polyphosphazene Materials," Ph.D. Thesis in Chemistrym Pennsylvania State University, Aug. 2007.
Barrett, Eric W., "Polyphosphazenes for Biomedical Divices and Other Applications," Ph.D. Thesis in Chemistry, Pennsylvania State University, Dec. 2005.
Guigley, Kevin S., "Hydrogen Bonded Polymer Blends," Ph.D. Thesis in Materials Science and Engineering, Pennsylvania State University, Dec. 2001.
Welna, Daniel Thomas, "Design, Synthesis, and Characterization of Polymeric Materials for uses in Energy Storage Applications," Ph.D. Thesis in Chemistry, Pennsylvania State University, Aug. 2006.

(Continued)

*Primary Examiner* — Brian Gulledge

(57) ABSTRACT

Particles are provided for use in therapeutic and/or diagnostic procedures. The particles include poly[bis(trifluoroethoxy)phosphazene] and/or a derivatives thereof which may be present throughout the particles or within an outer coating of the particles. The particles can also include a core having a hydrogel formed from an acrylic-based polymer. Such particles may be provided to a user in specific selected sizes to allow for selective embolization of certain sized blood vessels or localized treatment with an active component agent in specific clinical uses. Microspheres of the present invention may further be provided with physical and/or chemical enhancements within the particles' cores to enhance visualization of the embolized tissue using a variety of medical imaging modalities, including conventional radiography, fluoroscopy, tomography, computerized tomography, ultrasound, scintillation, magnetic resonance, or other imaging technologies.

17 Claims, 14 Drawing Sheets

(56) References Cited

U.S. PATENT DOCUMENTS

| | | |
|---|---|---|
| 4,728,570 A | 3/1988 | Ashman et al. |
| 4,798,876 A | 1/1989 | Gould et al. |
| 4,803,075 A | 2/1989 | Wallace et al. |
| 4,837,285 A | 6/1989 | Berg et al. |
| 4,849,285 A | 7/1989 | Dillon |
| 4,851,046 A | 7/1989 | Low et al. |
| 4,880,622 A | 11/1989 | Allcock et al. |
| 4,883,699 A | 11/1989 | Aniuk et al. |
| 4,902,511 A | 2/1990 | Kronman |
| 4,911,691 A | 3/1990 | Aniuk et al. |
| 4,912,141 A | 3/1990 | Kronman |
| 4,975,280 A | 12/1990 | Schacht et al. |
| 4,999,188 A | 3/1991 | Solodovnik et al. |
| 5,007,940 A | 4/1991 | Berg |
| 5,019,400 A | 5/1991 | Gombotz et al. |
| 5,137,875 A | 8/1992 | Tsunenaga et al. |
| 5,142,008 A | 8/1992 | Holle et al. |
| 5,143,724 A | 9/1992 | Leshchiner et al. |
| 5,158,573 A | 10/1992 | Berg |
| 5,162,430 A | 11/1992 | Rhee et al. |
| 5,204,382 A | 4/1993 | Wallace et al. |
| 5,238,569 A | 8/1993 | Soria et al. |
| 5,258,028 A | 11/1993 | Ersek et al. |
| 5,278,201 A | 1/1994 | Dunn et al. |
| 5,278,202 A | 1/1994 | Dunn et al. |
| 5,292,802 A | 3/1994 | Rhee et al. |
| 5,294,446 A | 3/1994 | Schlameus et al. |
| 5,304,595 A | 4/1994 | Rhee et al. |
| 5,306,500 A | 4/1994 | Rhee et al. |
| 5,308,701 A | 5/1994 | Cohen et al. |
| 5,324,775 A | 6/1994 | Rhee et al. |
| 5,342,557 A | 8/1994 | Kennedy |
| 5,344,452 A | 9/1994 | Lemperle |
| 5,352,715 A | 10/1994 | Wallace et al. |
| 5,368,859 A | 11/1994 | Dunn et al. |
| 5,395,620 A | 3/1995 | Huc et al. |
| 5,397,352 A | 3/1995 | Burres |
| 5,399,351 A | 3/1995 | Leshchiner et al. |
| 5,413,791 A | 5/1995 | Rhee et al. |
| 5,428,024 A | 6/1995 | Chu et al. |
| 5,439,446 A | 8/1995 | Barry |
| 5,446,091 A | 8/1995 | Rhee et al. |
| 5,451,406 A | 9/1995 | Lawin et al. |
| 5,456,693 A | 10/1995 | Conston et al. |
| 5,476,666 A | 12/1995 | Rhee et al. |
| 5,487,390 A | 1/1996 | Cohen et al. |
| 5,487,897 A | 1/1996 | Polson et al. |
| 5,494,673 A | 2/1996 | Andrianov et al. |
| 5,494,682 A | 2/1996 | Cohen et al. |
| 5,500,161 A | 3/1996 | Andrianov et al. |
| 5,510,418 A | 4/1996 | Rhee et al. |
| 5,516,532 A | 5/1996 | Atala et al. |
| 5,529,777 A | 6/1996 | Andrianov et al. |
| 5,548,060 A | 8/1996 | Allcock et al. |
| 5,552,159 A | 9/1996 | Mueller et al. |
| 5,562,099 A | 10/1996 | Cohen et al. |
| 5,562,909 A | 10/1996 | Allcock et al. |
| 5,571,182 A | 11/1996 | Ersek et al. |
| 5,599,852 A | 2/1997 | Scopelianos et al. |
| 5,605,696 A | 2/1997 | Eury et al. |
| 5,624,685 A | 4/1997 | Takahashi et al. |
| 5,633,001 A | 5/1997 | Ågerup |
| 5,634,946 A | 6/1997 | Slepian |
| 5,635,215 A | 6/1997 | Boschetti et al. |
| 5,639,796 A | 6/1997 | Lee |
| 5,648,100 A | 7/1997 | Boschetti et al. |
| 5,681,873 A | 10/1997 | Norton et al. |
| 5,686,425 A | 11/1997 | Lee |
| 5,707,597 A | 1/1998 | Andrianov et al. |
| 5,716,981 A | 2/1998 | Hunter et al. |
| 5,728,752 A | 3/1998 | Scopelianos et al. |
| 5,733,562 A | 3/1998 | Lee |
| 5,752,974 A | 5/1998 | Rhee et al. |
| 5,755,658 A | 5/1998 | Wallace et al. |
| 5,763,399 A | 6/1998 | Lee |
| 5,776,193 A | 7/1998 | Kwan et al. |
| 5,788,979 A | 8/1998 | Alt et al. |
| 5,792,478 A | 8/1998 | Lawin et al. |
| 5,814,704 A | 9/1998 | Andrianov et al. |
| 5,824,333 A | 10/1998 | Scopelianos et al. |
| 5,840,290 A | 11/1998 | Hench et al. |
| 5,840,819 A | 11/1998 | Biensan |
| 5,855,895 A | 1/1999 | Andrianov et al. |
| 5,873,904 A | 2/1999 | Ragheb et al. |
| 5,886,026 A | 3/1999 | Hunter et al. |
| 5,914,388 A | 6/1999 | Allcock |
| 5,922,025 A | 7/1999 | Hubbard |
| 5,955,143 A | 9/1999 | Wheatley et al. |
| 5,962,427 A | 10/1999 | Goldstein et al. |
| 5,980,972 A | 11/1999 | Ding |
| 5,997,301 A | 12/1999 | Linden |
| 6,007,573 A | 12/1999 | Wallace et al. |
| 6,015,563 A | 1/2000 | Andrianov et al. |
| 6,063,061 A | 5/2000 | Wallace et al. |
| 6,066,325 A | 5/2000 | Wallace et al. |
| 6,071,530 A | 6/2000 | Polson et al. |
| 6,077,916 A | 6/2000 | Laurencin |
| 6,083,262 A | 7/2000 | Caravel |
| 6,165,489 A | 12/2000 | Berg et al. |
| 6,190,684 B1 | 2/2001 | Hench et al. |
| 6,207,171 B1 | 3/2001 | Payne et al. |
| 6,210,715 B1 | 4/2001 | Starling et al. |
| 6,214,331 B1 | 4/2001 | Vanderhoff et al. |
| 6,235,061 B1 | 5/2001 | Laurencin et al. |
| 6,254,634 B1 | 7/2001 | Anderson |
| 6,261,323 B1 | 7/2001 | Neto |
| 6,261,325 B1 | 7/2001 | de la Mettrie et al. |
| 6,261,573 B1 | 7/2001 | Loebelenz et al. |
| 6,270,748 B1 | 8/2001 | Annan et al. |
| 6,273,913 B1 | 8/2001 | Wright et al. |
| 6,277,392 B1 | 8/2001 | Klein |
| 6,281,015 B1 | 8/2001 | Mooney et al. |
| 6,284,284 B1 | 9/2001 | Naughton |
| 6,309,420 B1 | 10/2001 | Preissman |
| 6,319,984 B1 | 11/2001 | Song et al. |
| 6,335,028 B1 | 1/2002 | Vogel et al. |
| 6,335,383 B1 | 1/2002 | Scopelianos et al. |
| 6,346,110 B2 | 2/2002 | Wu |
| 6,365,187 B2 | 4/2002 | Mathiowitz et al. |
| 6,383,500 B1 | 5/2002 | Wooley et al. |
| 6,391,343 B1 | 5/2002 | Yen |
| 6,423,332 B1 | 7/2002 | Huxel et al. |
| 6,423,343 B1 | 7/2002 | Lee et al. |
| 6,431,174 B1 | 8/2002 | Knudson et al. |
| 6,432,128 B1 | 8/2002 | Wallace et al. |
| 6,432,437 B1 | 8/2002 | Hubbard |
| 6,436,424 B1 | 8/2002 | Vogel |
| 6,458,387 B1 | 10/2002 | Scott et al. |
| 6,458,889 B1 | 10/2002 | Trollsas et al. |
| 6,485,514 B1 | 11/2002 | Wrenn, Jr. |
| 6,491,903 B1 | 12/2002 | Forster et al. |
| 6,503,556 B2 | 1/2003 | Harish et al. |
| 6,506,411 B2 | 1/2003 | Hunter et al. |
| 6,530,878 B2 | 3/2003 | Silverman et al. |
| 6,531,152 B1 | 3/2003 | Lerner et al. |
| 6,537,574 B1 | 3/2003 | Hubbard |
| 6,544,503 B1 | 4/2003 | Vanderhoff et al. |
| 6,546,936 B2 | 4/2003 | Knudson et al. |
| 6,555,123 B2 | 4/2003 | Williams et al. |
| 6,558,612 B1 | 5/2003 | Hubbard |
| 6,569,195 B2 | 5/2003 | Yang et al. |
| 6,585,994 B2 | 7/2003 | Williams et al. |
| 6,620,185 B1 | 9/2003 | Harvie et al. |
| 6,652,575 B2 | 11/2003 | Wang |
| 6,652,873 B2 | 11/2003 | Deaver et al. |
| 6,660,301 B1 | 12/2003 | Vogel et al. |
| 6,662,805 B2 | 12/2003 | Frondoza et al. |
| 6,666,892 B2 | 12/2003 | Hiles et al. |
| 6,669,719 B2 | 12/2003 | Wallace et al. |
| 6,676,971 B2 | 1/2004 | Goupil et al. |
| 6,680,046 B1 | 1/2004 | Boschetti |
| 6,682,760 B2 | 1/2004 | Noff et al. |
| 6,689,823 B1 | 2/2004 | Bellare et al. |
| 6,699,471 B2 | 3/2004 | Radice et al. |

(56) References Cited

U.S. PATENT DOCUMENTS

| | | |
|---|---|---|
| 6,713,646 B2 | 3/2004 | Zhang et al. |
| 6,767,637 B2 | 7/2004 | Park et al. |
| 6,790,456 B2 | 9/2004 | Vogel et al. |
| 6,858,634 B2 | 2/2005 | Asrar et al. |
| 6,866,860 B2 | 3/2005 | Nathan |
| 6,869,445 B1 | 3/2005 | Johnson |
| 6,872,799 B2 | 3/2005 | Nathan |
| 6,884,905 B2 | 4/2005 | Zhang et al. |
| 6,916,910 B2 | 7/2005 | Wolfinbarger, Jr. |
| 6,933,326 B1 | 8/2005 | Griffey et al. |
| 6,936,271 B1 | 8/2005 | Oliver et al. |
| 6,949,251 B2 | 9/2005 | Dalal et al. |
| 6,962,979 B1 | 11/2005 | Rhee |
| 6,967,234 B2 | 11/2005 | Nathan |
| 7,004,977 B2 | 2/2006 | Ashman |
| 7,012,126 B2 | 3/2006 | Matsuda et al. |
| 7,025,980 B1 | 4/2006 | Williams et al. |
| 7,025,990 B2 | 4/2006 | Sawhney |
| 7,026,374 B2 | 4/2006 | Nathan et al. |
| 7,053,134 B2 | 5/2006 | Baldwin et al. |
| 7,053,209 B1 | 5/2006 | Gibson et al. |
| 7,056,277 B2 | 6/2006 | Silverman et al. |
| 7,057,019 B2 | 6/2006 | Pathak |
| 7,060,287 B1 | 6/2006 | Hubbard et al. |
| 7,060,298 B2 | 6/2006 | Vogel et al. |
| 7,077,144 B2 | 7/2006 | Knudson et al. |
| 7,094,369 B2 | 8/2006 | Buiser et al. |
| 7,129,209 B2 | 10/2006 | Rhee |
| 7,131,997 B2 | 11/2006 | Bourne et al. |
| 7,135,593 B2 | 11/2006 | Zhang et al. |
| 7,144,414 B2 | 12/2006 | Harvie et al. |
| 7,157,080 B2 | 1/2007 | Radice et al. |
| 7,160,931 B2 | 1/2007 | Cheng et al. |
| 7,192,984 B2 | 3/2007 | Berg et al. |
| 7,244,270 B2 | 7/2007 | Lesh |
| 7,249,601 B2 | 7/2007 | Silverman et al. |
| 7,265,199 B2 | 9/2007 | Grunze |
| 7,288,319 B2 | 10/2007 | Baldwin et al. |
| 7,303,756 B1 | 12/2007 | Bodmeier |
| 7,314,636 B2 | 1/2008 | Caseres et al. |
| 7,326,172 B2 | 2/2008 | Miller |
| 7,338,657 B2 | 3/2008 | Vogel et al. |
| 2001/0014717 A1 | 8/2001 | Hossainy et al. |
| 2001/0029351 A1 | 10/2001 | Faletico et al. |
| 2002/0005206 A1 | 1/2002 | Faletico et al. |
| 2002/0016637 A1 | 2/2002 | Anton |
| 2002/0068089 A1* | 6/2002 | Vogel .................. A61K 9/0034 424/490 |
| 2002/0094440 A1 | 7/2002 | Llanos et al. |
| 2002/0111590 A1 | 8/2002 | Davila et al. |
| 2002/0119202 A1 | 8/2002 | Hunter et al. |
| 2002/0133183 A1 | 9/2002 | Lentz et al. |
| 2002/0151466 A1 | 10/2002 | Hubbard et al. |
| 2002/0165608 A1 | 11/2002 | Llanos et al. |
| 2002/0197326 A1 | 12/2002 | Vogel et al. |
| 2003/0004568 A1 | 1/2003 | Ken et al. |
| 2003/0009968 A1 | 1/2003 | Libby et al. |
| 2003/0060877 A1 | 3/2003 | Falotico et al. |
| 2003/0065345 A1 | 4/2003 | Weadock |
| 2003/0065377 A1 | 4/2003 | Davila et al. |
| 2003/0140930 A1 | 7/2003 | Knudson et al. |
| 2003/0149490 A1 | 8/2003 | Ashman |
| 2003/0153806 A1 | 8/2003 | Miller |
| 2003/0153983 A1 | 8/2003 | Miller et al. |
| 2003/0153985 A1 | 8/2003 | Lee |
| 2003/0157142 A1 | 8/2003 | Nagel et al. |
| 2003/0171646 A1 | 9/2003 | Pratt et al. |
| 2003/0215519 A1 | 11/2003 | Schwarz et al. |
| 2004/0020497 A1 | 2/2004 | Knudson et al. |
| 2004/0028676 A1 | 2/2004 | Klein et al. |
| 2004/0047892 A1 | 3/2004 | Desrosiers et al. |
| 2004/0091425 A1 | 5/2004 | Boschetti |
| 2004/0096514 A1 | 5/2004 | Vogel et al. |
| 2004/0096969 A1 | 5/2004 | Grunze |
| 2004/0101564 A1 | 5/2004 | Rioux et al. |
| 2004/0117033 A1 | 6/2004 | Frondoza et al. |
| 2004/0142465 A1 | 7/2004 | Radice et al. |
| 2004/0185021 A1 | 9/2004 | Hubbard |
| 2004/0187878 A1 | 9/2004 | Knudson et al. |
| 2004/0210230 A1 | 10/2004 | Furlow |
| 2004/0241203 A1 | 12/2004 | Shakesheff et al. |
| 2005/0025708 A1 | 2/2005 | Vogel et al. |
| 2005/0037047 A1 | 2/2005 | Song |
| 2005/0136093 A1 | 6/2005 | Denk |
| 2005/0165203 A1 | 7/2005 | Kohn et al. |
| 2005/0208095 A1 | 9/2005 | Hunter et al. |
| 2005/0209629 A1 | 9/2005 | Kerr et al. |
| 2005/0234210 A1 | 10/2005 | Andrianov et al. |
| 2006/0008529 A1 | 1/2006 | Meyerhoff et al. |
| 2006/0067883 A1 | 3/2006 | Krom et al. |
| 2006/0088476 A1 | 4/2006 | Harder et al. |
| 2006/0147895 A1 | 7/2006 | Purdum |
| 2006/0201673 A1 | 9/2006 | Welton et al. |
| 2006/0240064 A9 | 10/2006 | Hunter et al. |
| 2006/0246109 A1 | 11/2006 | Hossainy et al. |
| 2006/0251582 A1 | 11/2006 | Reb |
| 2006/0251697 A1 | 11/2006 | Li et al. |
| 2007/0003503 A1 | 1/2007 | Sabetsky |
| 2007/0003584 A1 | 1/2007 | Anderson |
| 2007/0077544 A1 | 4/2007 | Lemperle et al. |
| 2007/0100449 A1 | 5/2007 | O'Neil et al. |
| 2007/0191964 A1 | 8/2007 | Preissman |
| 2007/0240725 A1 | 10/2007 | McKay |
| 2007/0292429 A1 | 12/2007 | Brady et al. |
| 2008/0003256 A1 | 1/2008 | Martens et al. |
| 2008/0015498 A1 | 1/2008 | Lesh |
| 2008/0058954 A1 | 3/2008 | Trieu |
| 2008/0102029 A1 | 5/2008 | Fritz et al. |

FOREIGN PATENT DOCUMENTS

| | | |
|---|---|---|
| DE | 10019982 | 10/2001 |
| DE | 10100961 | 8/2002 |
| EP | 0150699 | 8/1985 |
| EP | 0286709 A1 | 10/1988 |
| EP | 0706376 B1 | 6/1997 |
| EP | 0804909 A2 | 11/1997 |
| EP | 0970711 | 1/2000 |
| EP | 1488817 | 1/2002 |
| EP | 1179353 | 2/2002 |
| EP | 1112094 | 6/2003 |
| EP | 1337285 | 8/2003 |
| EP | 1426075 A | 6/2004 |
| JP | 58079915 | 5/1983 |
| JP | 62086024 A2 | 4/1987 |
| JP | 4337328 | 11/1992 |
| WO | WO 8809664 A1 | 12/1988 |
| WO | WO 9321858 A1 | 11/1993 |
| WO | WO 9502628 A1 | 1/1995 |
| WO | WO 9528966 | 11/1995 |
| WO | WO 9600103 | 1/1996 |
| WO | WO 9604015 A1 | 2/1996 |
| WO | WO 9625176 | 8/1996 |
| WO | WO 9625897 A2 | 8/1996 |
| WO | WO 9629059 | 9/1996 |
| WO | WO 9800531 A | 1/1998 |
| WO | WO 9843618 | 10/1998 |
| WO | WO 9852605 A1 | 11/1998 |
| WO | WO 9856312 A1 | 12/1998 |
| WO | WO 9909088 | 2/1999 |
| WO | WO 9916416 A2 | 4/1999 |
| WO | WO 9916477 | 4/1999 |
| WO | WO 9942147 | 8/1999 |
| WO | WO 9952356 A1 | 10/1999 |
| WO | WO 0032238 | 6/2000 |
| WO | WO 0056254 A | 9/2000 |
| WO | WO 0061204 | 10/2000 |
| WO | WO 0136008 A2 | 5/2001 |
| WO | WO 0145763 | 6/2001 |
| WO | WO 0149340 | 7/2001 |
| WO | WO 0170296 A1 | 9/2001 |
| WO | WO 01/72281 A2 | 10/2001 |
| WO | WO 0180919 | 11/2001 |
| WO | WO 0187368 | 11/2001 |

(56) References Cited

FOREIGN PATENT DOCUMENTS

| WO | WO 0187372 A1 | 11/2001 | | |
|---|---|---|---|---|
| WO | WO 0224247 A1 | 3/2002 | | |
| WO | WO 02/064666 | * | 8/2002 | ............ C08G 79/02 |
| WO | WO 02064666 | | 8/2002 | |
| WO | WO 03015719 A | | 2/2003 | |
| WO | WO 2004004795 A | | 1/2004 | |
| WO | WO 2004011055 A2 | | 2/2004 | |
| WO | WO 2004048432 A | | 6/2004 | |
| WO | WO 2004060283 A | | 7/2004 | |
| WO | WO 2006/046155 A2 | | 5/2006 | |
| WO | WO 2007/056316 A | | 5/2007 | |

OTHER PUBLICATIONS

Maher, Andrew Elessar, "Synthesis and Characterization of Mixed-Substituent Poly (Organophosphazenes)," Ph.D. Thesis in Chemistry, Pennsylvania State University, May 2004.
Nielsen, Gunmar D., et al., "Sensory irritation mechanisoms investigated from model compounds: trifluoroethanol, hexafluoroisopropanol and methyl hexafluoroisopropyl ether," 1996, Arch Toxicol, 70:319-328.
Kumar, Yogeshi, et al., "Molten-globule like partially folded states of human serum albumin induced by fluoro and alkyl alcohols at low pH," Archives of Biophysics, 426 (2004) 3-10.
Hansen, Charles M., "Hansen Solubility Parameters—A User's Handbook,"2000 by CRC Press LLC.
Gast, Klaus, et al., "Fluoroalcohol-induced structural changes of proteins: some aspects of cosolvent-protein interactions," Eur Biophys J (2001 20:273-283).
Kumar, Yogesh, et al., "Influence of Fluoro, Chloro and Alkyl Alcohols on the Folding Pathway of Human Serum Albumin," J. Biochem, (2005), 138, 335-341.
Rothemund, Sven, et al., "Temperature coefficients of amide proton NMR resonance frequencies in trifluoroethanol: A monitor of intramolecular hydrogen bonds in helical peptides?," Journal of Biomecular NMR, 8 91996) 93-97.
Yao, Shenggen, et al. "Peptide self-association in aqueous trifluoroethanol monitored by pulsed field gradient NMR diffusion measurements," Journal of Biomolecular NMR, 16:109-111, 2000.
Contreras, Miguel Angel, et al., "Temperature coefficients of peptides dissolved in hexafluoroisopropanol monitor distortions of helices," Letters in Peptide Science, 4 (1979) 29-39.
Roccatano, Danilo, et al., "Effect of hexafluoroisopropanol alcohol on the structure of melittin: A molecular dynamics simulation study," Protein Science, 2005, 14:2582-2589.
Hori, Yoshio, et al., Functional Analysis of the Tissue-Engineered Stomach Wall, Artificial Organs, 2002, 26 (10):868-893, Blackwell Publishing, Inc., International Society for Artificial Organs.
Allcock, Harry , R., et al., "Antibacterial activity and mutagenicity studies of water-soluble phosphazene high polymers," Biomaterials, vol. 13, No. 2, pp. 857-862 (1992), Butterworth-Heinemann Ltd., USA.
Mrowietz, C., et al., "Haemocompatibility of polymer-coated stainless steel stents as compared to uncoated stents," Clinical Hemorheology and Microcirculation, 32 (2005) 89-103.
Cohen, Smadar, et al., "Design of Synthetic Polymeric Structures for Cell Transplantation and Tissue Engineering." Clinical Materials, vol. 13, 3-10 91993), Elsevier Science Publishers Ltd., England.
Huang, Yangmin, et al., "Long-term biocompatibillity evaluation of a novel polymer-coated stent in a porcine coronary stent model," Therapy and prevention, 2003, Coronary Artery Disease, vol. 14, No. 5, 401-408.
Richter, Goetz M., et al., "A New Polymer Concept for Coating of Vascular Stents Using PTFEP (poly(bis(trifluoroethoxy)phosphazene) to Reduce Thrombogenicity and Late In-Stent Stenosis," Investigative Radiology, Apr. 2005, vol. 40, No. 4, 210-218.

Welle, Alexander, "Competitive plasma protein adsorption on modified polymer surfaces monitored by quartz crystal microbalance technique," J. Biomater. Sci. Polymer Edn. (2004) vol. 15, No. 3, pp. 357-370.
Welle, Alexander, et al., "Blood Compatibility of Poly[bis(trifluoroethoxy)phosphazene]," Institute of Applied Physical Chemistry, JAMP, vol. 4, 6-10, (2000), University fo Heidelberg, Germany.
Reichert, W. M., et al., "Polyphosphazenes: Effect of molecular motions on thrombogenesis," Journal of Biomedical Materials Research, (1982), vol. 16, 301-312.
Lopez, Gabriel P., et al., "Glow Discharge Plasma Deposition of Tetraethylene Glycol Dimethyl Ether for Fouling-Resistant Biomaterial Surfaces," J. of Biomedical Materials Research, vol. 26, 415-439 91992), John Wiley&Sons, Inc., USA.
Laurencin, Cato T., et al., "Use of polyphosphazenes for skeletal tissue regeneration,"J. Biomedical Materials Research, vol. 27, No. 7, pp. 963-973 (1993), John Wiley & Sons, Inc., USA.
IBIM, Sobrasua M., et al., "Controlled Macromolecule Release from Poly(phosphazene) Matrices," Journal of Controlled Release, vol. 40, 31-39 (Jun. 1996), Elsevier Science B.V.
Veronese, Francesco M., et al., "Polyphosphazene Membranes and microspheres in Periodontal Diseases and Implant Surgery," Biomaterials, vol. 20, 91-98 91999), Elsevier, USA.
Vinogradova, S.V., et al., "Open-chain Poly(organophosphazenes). Synthesis and Properties," Russian Chemical Reviews, vol. 67, 515-534 (1998), Russian Academy of Sciences and Turpion Ltd.
Welle, A., et al., "Plasma Protein Adsorption and Platelet Adhesion on Poly[bis(trifluoroethoxy) phosphazene] and reference material surfaces," appeared in J. Colloid Intef. Sci., 197, 263-274, (1998).
Barrett, Eric W., et al., "Patterning Poly(organophosphazenes) for Selective Cell Adhesion Applications," Biomacromolecules, (2005), 6, 1689-1697.
Acta Polymerica 37 (1986) No. 4: 203-208.
Acta Polymerica 30 (1979), pp. 245-248.
Acta Polymerica 36 (1985), pp. 627-631.
Kingshott, P., "Surfaces that Resist Bioadhesion," Current Opinion in Solid State and Materials Science, vol. 4, 403-412 (1999), Pergamon.
Waksman, R., "Vascular Brachytherapy: Applications in the Era of Drug-Eluting Stents," Reviews in Cardiovascular Medicine, vol. 2, S23-S30 (2002), MedReviews, LLC, USA.
Kajiwara, M., "The Study of the Cultivation of Chinese Hamster Ovary and Bows Cell Lines," Phosphorus, Sulfur, and Silicon, vol. 76, pp. 163-166 (1993), Gordon and Breach Scien.
Ph. Potin & R. DeJaeger, "Review: Polyphosphazenes: Synthesis, Structures, Properties, Applications," European Polymer Journal, vol. 27, 341-348 (991), Pergamon Press, Great Britain.
Lemmouchi, Y., et al., "Biodegradable Polyphosphazenes for Drug Delivery," Macromolecular Symposia, vol. 123, 103-112 (Sep. 1997) Wiley VCH, Weinheim, Germany.
"Making Better Magnetic Nanoparticles," Physorg.com, Science:Physics:Tech: nano:news;Source:National Cancer Institute.
Cui, et al., "Preparation of Controlled Releasing Acrylic Polymer Microspheres of Acebutolol Hydrochloride and Those Powder Coated Microspheres with Sodium Alginate in a Polymeric Spherical Crystallization System," Che. Phar. Bull., (1990), vol. 44, No. 4, pp. 837-842 (Abstract only).
Hart, et al., "Poly(methylmethacrylate) Suspension Polymer," Macromolecular Syntheses, Collective vol. 1, pp. 23-25.
Kumbar, Sangamesh G., et al., In Vitro and In Vivo Characterization of Biodegradable Poly(organophosphazenes) for Biomedical Applications, Journal of Inorganic and Organometallic Polymers and Materials, vol. 16, No. 4, Dec. 2006, pp. 365-385.
Jayakrishnan, et al., "Hydrogel microspheres from crosslinked poly(methyl methacrylate): synthesis and biocompatibility studies," Bull. Mater. Sci., Mar. 1989, vol. 12, No. 1, pp. 17-25.
Phadke, et al., "Embolization of Cranial/Spinal Tumors and Vascular Malformations with Hydrogel Microspheres," Acta Radiologica, 2002, vol. 43, pp. 15-20.
Rao, et al., "Hydrolysed microspheres From Cross-Linked Polymethyl Methacrylate(Hydrogel)," J. Neuroradiol, 1991, vol. 18, pp. 61-69.

(56) References Cited

OTHER PUBLICATIONS

Allcock, Harry R., Poly(organophosphazenes)-Unusual New High Polymers, Angew. Chem. Int. Ed. Engl. 16, 147-156 (1977).
Thanoo, et al., "Preparation of Hydrogel Beads from Crosslinked Poly(Methyl Methacrylate) Microspheres by Alkaline Hydrolysis," J. Appl. P. Sci., vol. 39, pp. 1153-1161 (1990) (Abstract only).
De Jaeger, Roger, et al., "Poly(organophosphazene)s and Related Compounds: Synthesis, Properties and Applications," Prog. Polym. Sci., vol. 23, 179-276 (1998), Pergamon Press, Great Britain.
De Scheerder, Ivan K., et al., "Angiopeptin Loaded Stents Inhibit the Neointimal Reaction Induced by Polymer Coated Stents Implanted in Porcine Coronary Arteries," Abstract 772-6, 99. 286A, JACC (Feb. 1995). (Abstract).
Grunze, Michael, et al., 32P-Labeled polyphosphazenes, 1999, Chemical Abstracts, vol. 130, No. 20: 272061.
Macromolecules 1987, vol. 20, pp. 782-789.
Mark, James E., et al., "Polyphosphazenes," Inorganic Polymers, 1992, pp. 61-139, XP000866367, pp. 95-117.
McCaffrey, R.R. et al., "Synthesis, Casting, and Diffusion Testing of Poly[bis(tri-fluoroethoxy)phosphazene] Membranes," J. of Membrane Science, vol. 28, 47-67 (1986), Elsevier Science Publishers B.V., Netherlands.
Welle, A. et al., "Polyphosphazenes as antithrombotic coatings for prostetic heart valves," Presented at 19th Annual Meeting of the Adhesion Society, Myrtle Beach, SC, 4 pages.
Honarkar, Hengameh, et al., "Applications of Inorganic Polymeric Materials, III: Polyphosphazenes," Monatshefte fur Chemie 138, 923-933 (2007).
Allcock, H., "Phosphazene high polymers with bioactive substitutent groups: prospective anesthetic aminophosphazenes," Macromolecules, 15(3):689-693 (1982).
Ambrosio, et al., "Novel Polyphosphazene-Hydroxyapatite Composites as Biomaterials," IEEE Engineering in Medicine and Biology Magazine, 22(5):18-26 (Sep. 5, 2003).
Champion, J., et al., "Particle shape: A new design parameter for micro-and nanoscale drug delivery carriers, "Journal of Controlled Release, 121 (2007) 3-9.

Chaubal, M., et al., "Polyphosphates and other phosphorus-containing polymers for drug delivery applications," Therapeutic Drug Carrier Systems, 20(4):295-315 (2003).
El-Amin, et al., "The Biocompatibility of Biodegradable Glycine Containing Polyphosphazenes: A Comparative Study in Bone," Journal of Inorganic and Organometallic Polymers and Materials, 2006, vol. 16, No. 4, pp. 387-396.
Goedemoed, J., et al., "Development of implantable antitumor devices based on polyphosphazenes," Die Makromolekulare Chemie, 19:341-365 (1988).
Henry, R., et al., "Topical lidocaine-prolocaine spray for the treatment of premature ejaculation," International Journal of Impotence Research, 15(4):277-281 (2003).
Laurencin, C., et al., "Controlled release using a new bioerodible polyphosphazene matrix system," Journal of Biomedical Materials Research, 21:1231-1246 (1987).
International Search Report and Written Opinion (PCT/US2007/082426), International Searching Authority.
International Search Report and Written Opinion (PCT/US2007/082430), International Searching Authority.
International Search Report and Written Opinion (PCT/US2007/082672), International Searching Authority.
International Search Report and Written Opinion (PCT/US2007/083043), International Searching Authority.
International Search Report and Written Opinion (PCT/US2007/083199), International Searching Authority.
International Search Report and Written Opinion (PCT/US2007/083209), International Searching Authority.
International Search Report and Written Opinion (PCT/US2007/083216), International Searching Authority.
International Search Report and Written Opinion (PCT/US2007/082659), International Searching Authority.
Caliceti, Paolo, et al., "Polyphosphazene microspheres for insulin delivery," International Journal of Pharmaceutics, 211 (2000) 57-65.
International Search Report and Written Opinion (PCT/US2007/080969), International Searching Authority.

* cited by examiner

File Name=ptfep1_8.tif 100μm  EHT=10.000kV  Date:16 Jan 2004
Mag=100X ⊢―――⊣         Photo No.=3280  Time:8:47:17

Experimental cryoextraction setup

| Legend | Typical dimensions |
|---|---|
| A | Drop distance length | 5-10 cm |
| B | Liq. Nitrogen layer depth | 5-10 cm |
| C | Nonsolvent layer depth | 1-2 cm |
| D | Nonsolvent | |
| E | Solvent | |
| F | Syringe needle tip | (25G-33G) |
| G | Dewar | (1-2 l volume) |
| H | Lid | |
| I | Teflon tubing | (0.8mm dia.;40cm length) |

Cryovessel

| Legend | |
|---|---|
| J | Pump housing |
| K | Syringe |
| L | Teflon distributor with Teflon tubing attached |

Syringe Pump

10μm  EHT=3.00kV  Signal A=SE2  Date:21 Apr 2006
Mag=1.00kX ⊢——⊣  WD=5mm  Photo No.=7212  Time:8:38:21

100 nm  EHT=3.00kV  Signal A=SE2  Date:21 Apr 2005
Mag=50.00kX ⊢—⊣  WD=4mm  Photo No.=7258  Time:9:20:13

10μm   EHT=3.00kV   Signal A=InLens   Date:21 Jan 2005
Mag=1.00kX ⊢———⊣ WD=5mm   Photo No.=7296   Time:9:58:54

2μm   EHT=3.00kV   Signal A=InLens   Date:21 Apr 2005
Mag=5.00kX ⊢—⊣ WD=5mm   Photo No.=7299   Time:10:00:41

LOADABLE POLYMERIC PARTICLES FOR ENHANCED IMAGING IN CLINICAL APPLICATIONS AND METHODS OF PREPARING AND USING THE SAME

CROSS-REFERENCE TO RELATED APPLICATIONS

This application is a continuation-in-part of U.S. patent application Ser. No. 11/257,535, filed Oct. 25, 2005, which claims the benefit of priority under 35 U.S.C. §119(e) of U.S. Provisional Patent Applications Nos. 60/684,307, filed May 24, 2005 and 60/621,729, filed Oct. 25, 2004, the entire disclosures of which are incorporated herein by reference.

BACKGROUND OF THE INVENTION

Small particles, including microspheres and nanospheres, have many medical uses in diagnostic and/or therapeutic procedures. In selected clinical applications, it may be advantageous to provide such microspheres and nanospheres with physical and/or chemical qualities to enhance their visual identification using various clinical imaging modalities to make the in vivo location of such microspheres apparent to a user. Such microspheres and nanospheres may allow for selective embolization of certain sized blood vessels under visual control using various clinical imaging modalities in specific clinical uses.

Most particles used in medical applications are characterized by numerous disadvantages including irritation of the tissues with which they come in contact and initiation of adverse immune reactions. Additionally, many of the materials used to prepare these particles may degrade relatively rapidly within the mammalian body, thereby detracting from their utility in certain procedures where long term presence of intact particles may be necessary. Moreover, the degradation of these materials may release toxic or irritating compounds causing adverse reactions in the patients.

Some known particle types suffer from difficulties in achieving desirable suspension properties when such particles are incorporated into a delivery suspension for injection into a site in the body to be treated. Many times, the particles settle out or tend to "float" in the solution such that they are not uniformly suspended for even delivery. Furthermore, particles may tend to aggregate within the delivery solution and/or adhere to some part of the delivery device, making it necessary to compensate for these adhesive/attractive forces.

In order to achieve a stable dispersion, suitable dispersing agents may be added, which may include surfactants directed at breaking down attractive particle interactions. Depending on the nature of the particle interaction, materials such as the following may be used: cationic, anionic, or nonionic surfactants such as Tween™ 20, Tween™ 40, Tween™ 80, polyethylene glycols, sodium dodecyl sulfate, various naturally occurring proteins such as serum albumin, or any other macromolecular surfactants in the delivery formulation. Furthermore thickening agents can be used help prevent particles from settling by sedimentation and to increase solution viscosity, for example, polyvinyl alcohols, polyvinyl pyrrolidones, sugars, or dextrins. Density additives may also be used to achieve buoyancy.

It can also be difficult to visualize microparticles in solution to determine their degree of suspension when using clear, transparent polymeric acrylate hydrogel beads in aqueous suspension. The inert precipitate barium sulfate may be used in particle form an additive for bone cement, for silicones, for rendering items visible during X-ray examination and for providing radiopacity to polymeric acrylate particles. See Jayakrishnan et al., Bull. Mat. Sci., Vol. 12, No. 1, pp. 17-25 (1989). Barium sulfate also is known for improving fluidization, and is often used as an inorganic filler to impart anti-stick behavior to moist, aggregated particles. Other attempts to increase visualization of microparticles include the use of gold, for example, in Embosphere Gold™, which provides a magenta color to acrylate microparticles using small amounts of gold.

In certain medical applications, it may be of further value to provide microparticles such as microspheres in one or more sizes. Furthermore, it may also be of value to provide each of such sizes of microspheres incorporated with color-coded associated dyes to indicate the microsphere size to the user. In yet other applications of use, it may further be of value to provide sized and color-coded microspheres to a user in similarly color-coded syringes or other containers for transport and delivery to further aid a user in identifying the size of microspheres being used.

There thus exists in the art a need for small particles that can be formed to have a preferential generally spherical configuration for certain applications such as various therapeutic and diagnostic procedures which are not degraded by the natural systems of the mammalian system, are biocompatible, are easy to visualize in suspension while in use and/or demonstrate acceptable physical and suspension properties.

BRIEF SUMMARY OF THE INVENTION

This invention includes a particle for use in a therapeutic and/or diagnostic clinical procedure. The particle comprises poly[bis(trifluoroethoxy)phosphazene] and/or a derivative thereof.

The present invention further includes particles comprising poly[bis(trifluoroethoxy)phosphazene and/or a derivative thereof provided as microspheres provided in one or more specified sizes.

The present invention further includes particles comprising poly[bis(trifluoroethoxy)phosphazene] and/or a derivative thereof provided as sized microspheres and further comprising a color-coded dye incorporated into or attached to the exterior of the microspheres to visually aid a user in identifying the size of microspheres in use.

Microspheres of the present invention may further be provided as sized microspheres further comprising a color-coded dye incorporated into or attached to the exterior of the microspheres and contained or delivered in a similarly color-coded syringe or other transport or delivery container to further visually aid a user in providing a visual confirmation of the specific size of microspheres in use.

Also included is a method of minimizing blood flow to a tissue in a mammal comprising occluding at least a portion of a blood vessel of the mammal with at least one particle, wherein the particle comprises a poly[bis(trifluoroethoxy)phosphazene] and/or a derivative thereof.

Further described herein is a method of delivering an active agent to a localized area within a body of a mammal comprising contacting the localized area with at least one of a particle comprising poly[bis(trifluoroethoxy)phosphazene] and/or a derivative thereof and an active agent, such that an effective amount of the active agent is exposed to the localized area.

Also within the invention is a sustained release formulation of an active agent for oral administration, the formulation comprising a polymer capsule and an active agent, wherein the polymeric capsule comprises poly[bis(trifluoroethoxy)phosphazene] and/or a derivative thereof.

The invention further includes a method of tracing the passage of a particle through a blood vessel in a mammal, the method comprising injecting into the bloodstream of a mammal at least one tracer particle, the tracer particle comprising poly[bis(trifluoroethoxy)phosphazene] and/or a derivative thereof and a contrast agent, and imaging the route of the particle.

Also further described herein is a method of delivering a contrast agent for magnetic resonance imaging (MRI) to a localized area within a body of a mammal comprising contacting the localized area with at least one of a particle comprising poly[bis(trifluoroethoxy)phosphazene] and/or a derivative thereof and a contrast agent for magnetic resonance imaging, such that the presence of such particles may be identified and evaluated using magnetic resonance imaging techniques.

The invention further includes a method of tracing the passage of a particle through a blood vessel in a mammal, the method comprising injecting into the bloodstream of a mammal at least one tracer particle, the tracer particle comprising poly[bis(trifluoroethoxy)phosphazene] and/or a derivative thereof and a radioisotope, and imaging the route of the particle using scintillation or other radiation sensing imaging modalities.

Additionally, a method of enhanced ultrasound imaging is described herein. The method comprises administering to an ultrasound subject at least one particle comprising poly[bis(trifluoroethoxy)phosphazene] and/or a derivative thereof and a core containing one or more gas filled microbubbles to an area of the ultrasound subject to enhance echogenicity therein, and imaging the area of the subject using ultrasound.

The invention also includes a method of delivering an active agent to a localized area within the body of a mammal comprising contacting the localized area with at least one of a particle comprising poly[bis(trifluoroethoxy)phosphazene] and/or a derivative thereof and an active agent, such that an effective amount of the active agent is exposed to the localized area, wherein the particle comprises an agent to increase density.

The invention also includes a method of delivering a radiographic contrast agent to a localized area within the body of a mammal comprising contacting the localized area with at least one of a particle comprising poly[bis(trifluoroethoxy)phosphazene] and/or a derivative thereof and a radiographic contrast agent, such that the location of a plurality of the particles may be seen using conventional radiographic imaging techniques, including but not limited to plain radiographs, x-ray tomography, and computerized axial tomography.

Further, a method of minimizing agglomeration of particles formed from acrylic-based polymers is described in which the method comprises providing barium sulfate to the core and/or surface of the particles.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments that are presently preferred. It should be understood, however, that the invention is not limited to the precise arrangements and instrumentalities shown.

In the drawings:

FIG. 3A shows a 4× optical microscope view and FIG. 3B shows a 100× scanning electron microscope view;

FIG. 5A is an image obtained using an atomic force microscope and FIG. 5B is a scanning electron micrograph showing the surface of an unloaded polyphosphazene microsphere at 5000× magnification;

FIGS. 6 and 7 show a cryoextraction setup for use in an embodiment of the invention wherein FIG. 6 is a cryoextraction vessel and FIG. 7 is a syringe pump;

FIG. 11A is a 50× magnification of a minor amount of delamination in the strong white contrast portion. FIG. 11B is a 200× magnification of the microparticles of FIG. 11A. FIGS. 11C and 11D are, respectively, 200× and 1.0K× magnified SEMs of other Sample C microparticles showing only minor defects.

FIG. 12A is a conceptual representation of a selective embolization of an exemplary tumor mass by intravascular administration of microspheres. FIG. 12B shows an exemplary particle of the present invention comprising a polyphosphazene-coated microsphere further comprising a core with a gas-filled microbubble for enhanced visibility of sonography.

DETAILED DESCRIPTION OF THE INVENTION

Figure 1:
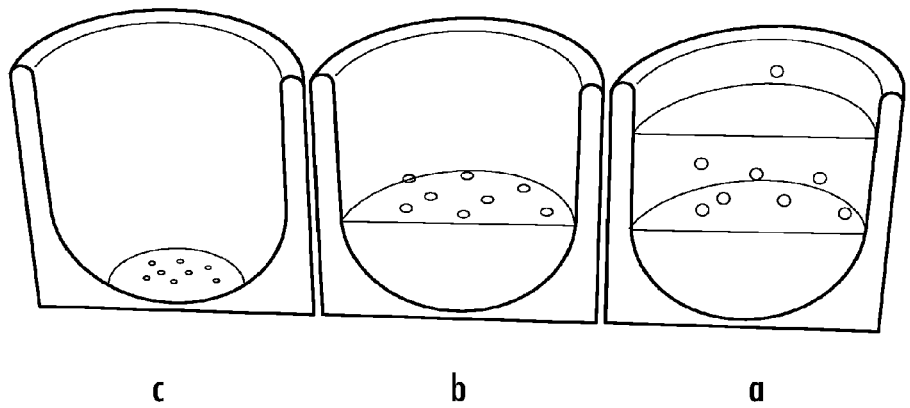
FIG. 1 shows a schematic representation of a general cryoextraction scheme used to prepare particles according to one embodiment of the invention.

Described herein are particles that may be manufactured using poly[bis(trifluoroethoxy)phosphazene] and/or derivatives thereof, as well as methods of preparing such particles. Additionally, described herein are therapeutic and/or diagnostic methods and procedures which use the particles as described herein, including methods of embolization using the particles, methods of delivery of an active agent using the particle (either orally or locally), methods of tracing or visualizing blood or other biological fluids through the body using the particles, methods of enhanced ultrasound (sonography) using the particles, and the like.

Also included are sustained release drug delivery formulations for oral administration including the particles for localized delivery of an active agent to the gastrointestinal system and/or systemic delivery of an active agent as well as a sustained release drug delivery formulation that can be injected subcutaneously or intravenously for localized delivery of an active agent.

All of the methods, compositions and formulations of the invention utilize at least one particle as described herein. "Particle" and "particles" as used herein mean a substantially spherical or ellipsoid article(s), hollow or solid, that may have any diameter suitable for use in the specific methods and applications described below, including a microsphere(s) and a nanosphere(s), beads and other bodies of a similar nature known in the art.

The preferred particles of the invention according to one embodiment described herein are composed, in whole or in part, the specific polyphosphazene polymer known as poly[bis(trifluoroethoxy)phosphazene] or a derivative of poly[bis(trifluoroethoxy)phosphazene].

Use of this specific polymer provides particles that are at least in part inorganic in that they include an inorganic polymer backbone and which are also biocompatible in that when introduced into a mammal (including humans and animals), they do not significantly induce a response of the specific or non-specific immune systems. The scope of the invention also includes the use(s) of such particles as controlled drug delivery vehicles or tracer particles for the visualization of blood vessels and other organs.

The particles are useful in a variety of therapeutic and/or diagnostic procedures in part because they can be prepared in sizes large enough to occlude a blood vessel as well as small enough to easily pass through the smaller vessels, for example, visualization or drug delivery purposes. Additionally, owing to the biocompatible nature of the polymer, the particles facilitate avoidance or elimination of immunogenic reactions generally encountered when foreign bodies are introduced into a mammalian body, such as "implant rejection" or "allergic shock," and other adverse reactions of the immune system. Moreover, it has been found that the particles of the invention exhibit reduced biodegradation in vivo, thereby increasing the long-term stability of the particle in the biological environment. Moreover, in those situations where some degradation is undergone by the polymer in the particle, the products released from the degradation include only non-toxic concentrations of phosphorous, ammonia, and trifluoroethanol, which, advantageously, is known to promote anti-inflammatory responses when in contact with mammalian tissue.

Each of the particles in the invention is formed at least in part of the polymer, poly[bis(2,2,2-trifluoroethoxy)phosphazene] or a derivative thereof (referred to further herein as "poly[bis(trifluoroethoxy)phosphazene]". As described herein, the polymer poly[bis(2,2,2-trifluoroethoxy)phosphazene] or derivatives thereof have chemical and biological qualities that distinguish this polymer from other know polymers in general, and from other know polyphosphazenes in particular. In one aspect of this invention, the polyphosphazene is poly[bis(2,2,2-trifluoroethoxy)phosphazene] or derivatives thereof, such as other alkoxide, halogenated alkoxide, or fluorinated alkoxide substituted analogs thereof. The preferred poly[bis(trifluoroethoxy) phosphazene]polymer is made up of repeating monomers represented by the formula (I) shown below:

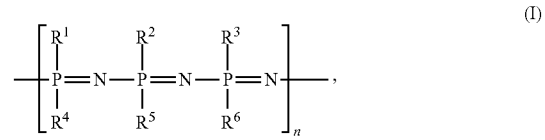

wherein $R^1$ to $R^6$ are all trifluoroethoxy ($OCH_2CF_3$) groups, and wherein n may vary from at least about 40 to about 100,000, as disclosed herein. Alternatively, one may use derivatives of this polymer in the present invention. The term "derivatives" is meant to refer to polymers made up of monomers having the structure of formula I but where one or more of the $R^1$ to $R^6$ functional group(s) is replaced by a different functional group(s), such as an unsubstituted alkoxide, a halogenated alkoxide, a fluorinated alkoxide, or any combination thereof, or where one or more of the $R^1$ to $R^6$ is replaced by any of the other functional group(s) disclosed herein, but where the biological inertness of the polymer is not substantially altered.

In one aspect of the polyphosphazene of formula (I) illustrated above, for example, at least one of the substituents $R^1$ to $R^6$ can be an unsubstituted alkoxy substituent, such as methoxy ($OCH_3$), ethoxy ($OCH_2CH_3$) or n-propoxy ($OCH_2CH_2CH_3$). In another aspect, for example, at least one of the substituents $R^1$ to $R^6$ is an alkoxy group substituted with at least one fluorine atom. Examples of useful fluorine-substituted alkoxy groups $R^1$ to $R^6$ include, but are not limited to $OCF_3$, $OCH_2CF_3$, $OCH_2CH_2CF_3$, $OCH_2CF_2CF_3$, $OCH(CF_3)_2$, $OCCH_3(CF_3)_2$, $OCH_2CF_2CF_2CF_3$, $OCH_2(CF_2)_3CF_3$, $OCH_2(CF_2)_4CF_3$, $OCH_2(CF_2)_5CF_3$, $OCH_2(CF_2)_6CF_3$, $OCH_2(CF_2)_7CF_3$, $OCH_2CF_2CHF_2$, $OCH_2CF_2CF_2CHF_2$, $OCH_2(CF_2)_3CHF_2$, $OCH_2(CF_2)_4CHF_2$, $OCH_2(CF_2)_5CHF_2$, $OCH_2(CF_2)_6CHF_2$, $OCH_2(CF_2)_7CHF_2$, and the like. Thus, while trifluoroethoxy ($OCH_2CF_3$) groups are preferred, these further exemplary functional groups also may be used alone, in combination with trifluoroethoxy, or in combination with each other. In one aspect, examples of especially useful fluorinated alkoxide functional groups that may be used include, but are not limited to, 2,2,3,3,3-pentafluoropropyloxy ($OCH_2CF_2CF_3$), 2,2,2,2',2',2'-hexafluoroisopropyloxy ($OCH(CF_3)_2$), 2,2,3,3,4,4,4-heptafluorobutyloxy ($OCH_2CF_2CF_2CF_3$), 3,3,4,4,5,5,6,6,7,7,8,8,8-tridecafluorooctyloxy ($OCH_2(CF_2)_7CF_3$), 2,2,3,3,-tetrafluoropropyloxy ($OCH_2CF_2CHF_2$), 2,2,3,3,4,4-hexafluorobutyloxy ($OCH_2CF_2CF_2CHF_2$), 3,3,4,4,5,5,6,6,7,7,8,8-dodecafluorooctyloxy ($OCH_2(CF_2)_7CHF_2$), and the like, including combinations thereof.

Further, in some embodiments, 1% or less of the $R^1$ to $R^6$ groups may be alkenoxy groups, a feature that may assist in crosslinking to provide a more elastomeric phosphazene polymer. In this aspect, alkenoxy groups include, but are not limited to, $OCH_2CH=CH_2$, $OCH_2CH_2CH=CH_2$, allylphenoxy groups, and the like, including combinations thereof. Also in formula (I) illustrated herein, the residues $R^1$ to $R^6$ are each independently variable and therefore can be the same or different.

By indicating that n can be as large as Go in formula I, it is intended to specify values of n that encompass polyphosphazene polymers that can have an average molecular weight of up to about 75 million Daltons. For example, in one aspect, n can vary from at least about 40 to about 100,000. In another aspect, by indicating that n can be as large as ∞ in formula I, it is intended to specify values of n from about 4,000 to about 50,000, more preferably, n is about 7,000 to about 40,000 and most preferably n is about 13,000 to about 30,000.

In another aspect of this invention, the polymer used to prepare the polymers disclosed herein has a molecular weight based on the above formula, which can be a molecular weight of at least about 70,000 g/mol, more preferably at least about 1,000,000 g/mol, and still more preferably a molecular weight of at least about $3 \times 10^6$ g/mol to about $20 \times 10^6$ g/mol. Most preferred are polymers having molecular weights of at least about 10,000,000 g/mol.

In a further aspect of the polyphosphazene formula (I) illustrated herein, n is 2 to ∞, and $R^1$ to $R^6$ are groups which are each selected independently from alkyl, aminoalkyl, haloalkyl, thioalkyl, thioaryl, alkoxy, haloalkoxy, aryloxy, haloaryloxy, alkylthiolate, arylthiolate, alkylsulphonyl, alkylamino, dialkylamino, heterocycloalkyl comprising one or more heteroatoms selected from nitrogen, oxygen, sulfur, phosphorus, or a combination thereof, or heteroaryl comprising one or more heteroatoms selected from nitrogen, oxygen, sulfur, phosphorus, or a combination thereof. In this aspect of formula (I), the pendant side groups or moieties (also termed "residues") $R^1$ to $R^6$ are each independently variable and therefore can be the same or different. Further, $R^1$ to $R^6$ can be substituted or unsubstituted. The alkyl groups or moieties within the alkoxy, alkylsulphonyl, dialkylamino, and other alkyl-containing groups can be, for example, straight or branched chain alkyl groups having from 1 to 20 carbon atoms, typically from 1 to 12 carbon atoms, it being possible for the alkyl groups to be further substituted, for example, by at least one halogen atom, such as a fluorine atom or other functional group such as those noted for the $R^1$ to $R^6$ groups above. By specifying alkyl groups such as propyl or butyl, it is intended to encompass any isomer of the particular alkyl group.

In one aspect, examples of alkoxy groups include, but are not limited to, methoxy, ethoxy, propoxy, and butoxy groups, and the like, which can also be further substituted. For example the alkoxy group can be substituted by at least one fluorine atom, with 2,2,2-trifluoroethoxy constituting a useful alkoxy group. In another aspect, one or more of the alkoxy groups contains at least one fluorine atom. Further, the alkoxy group can contain at least two fluorine atoms or the alkoxy group can contain three fluorine atoms. For example, the polyphosphazene that is combined with the silicone can be poly[bis(2,2,2-trifluoroethoxy)phosphazene]. Alkoxy groups of the polymer can also be combinations of the aforementioned embodiments wherein one or more fluorine atoms are present on the polyphosphazene in combination with other groups or atoms.

Examples of alkylsulphonyl substituents include, but are not limited to, methylsulphonyl, ethylsulphonyl, propylsulphonyl, and butylsulphonyl groups. Examples of dialkylamino substituents include, but are not limited to, dimethyl-, diethyl-, dipropyl-, and dibutylamino groups. Again, by specifying alkyl groups such as propyl or butyl, it is intended to encompass any isomer of the particular alkyl group.

Exemplary aryloxy groups include, for example, compounds having one or more aromatic ring systems having at least one oxygen atom, non-oxygenated atom, and/or rings having alkoxy substituents, it being possible for the aryl group to be substituted for example by at least one alkyl or alkoxy substituent defined above. Examples of aryloxy groups include, but are not limited to, phenoxy and naphthoxy groups, and derivatives thereof including, for example, substituted phenoxy and naphthoxy groups.

The heterocycloalkyl group can be, for example, a ring system which contains from 3 to 10 atoms, at least one ring atom being a nitrogen, oxygen, sulfur, phosphorus, or any combination of these heteroatoms. The hetereocycloalkyl group can be substituted, for example, by at least one alkyl or alkoxy substituent as defined above. Examples of heterocycloalkyl groups include, but are not limited to, piperidinyl, piperazinyl, pyrrolidinyl, and morpholinyl groups, and substituted analogs thereof.

The heteroaryl group can be, for example, a compound having one or more aromatic ring systems, at least one ring atom being a nitrogen, an oxygen, a sulfur, a phosphorus, or any combination of these heteroatoms. The heteroaryl group can be substituted for example by at least one alkyl or alkoxy substituent defined above. Examples of heteroaryl groups include, but are not limited to, imidazolyl, thiophene, furan, oxazolyl, pyrrolyl, pyridinyl, pyridinolyl, isoquinolinyl, and quinolinyl groups, and derivatives thereof, such as substituted groups.

The diameter of a particle formed according to the invention will vary depending on the end application in which the particle is to be used. The diameter of such particles is preferably about 1 to about 5,000 μm, with a diameter of about 1 to about 1,000 μm being most preferred. Other preferred sizes include diameters of about 200 to about 500 μm, about 1 to about 200 μm and greater than about 500 μm. In methods using the particle where more than one particle is preferred it is not necessary that all particles are of the same diameter or shape.

The particles may also include other compounds which function to enhance, alter or otherwise modify the behavior of the polymer or particle either during its preparation or in its therapeutic and/or diagnostic use. For example, active agents such as peptides, proteins, hormones, carbohydrates, polysaccharides, nucleic acids, lipids, vitamins, steroids and organic or inorganic drugs may be incorporated into the particle. Excipients such as dextran, other sugars, polyethylene glycol, glucose, and various salts, including, for example, chitosan glutamate, may be included in the particle.

Additionally, if desired, polymers other than the poly[bis (trifluoroethoxy)phosphazene] and/or its derivative may be included with in the particle. Examples of polymers may include poly(lactic acid), poly(lactic-co-glycolic acid), poly (caprolactone), polycarbonates, polyamides, polyanhydrides, polyamino acids, polyorthoesters, polyacetals, polycyanoacrylates, and polyurethanes. Other polymers include polyacrylates, ethylene-vinyl acetate co-polymers, acyl substituted cellulose acetates and derivatives thereof, degradable or non-degradable polyurethanes, polystyrenes, polyvinylchloride, polyvinyl fluoride, poly(vinyl imidazole), chlorosulphonated polyolefins, and polyethylene oxide. Examples of polyacrylates include, but are not limited to, acrylic acid, butyl acrylate, ethylhexyl acrylate, methyl acrylate, ethyl acrylate, acrylonitrile, methyl methacrylate, TMPTA (trimethylolpropane triacrylate), and the like. One may incorporate the selected compounds by any means known in the art, including diffusing, inserting or entrapping the additional compounds in the matrix of an already formed particle or by adding the additional compound to a polymer melt or to a polymer solvent in the preparation of the particle such as described herein.

The loaded or unloaded particle may be coated with an additional polymer layer or layers, including polymers such as those mentioned hereinabove. Further, poly[bis(trifluoroethoxy)phosphazene or its derivatives may be used to form such a coating on a particle formed of other suitable polymers or copolymers known or to be developed in the art that are used to form particles as described herein. Preferably, when coating a particle such as a microparticle, poly[bis(trifluoroethoxy)phosphazene is applied as a coating on a microparticle(s) formed of an acrylic-based polymer as set forth in further detail below.

Coatings are beneficial, for example, if the particle(s) are to be used in a sustained release, orally administered, drug delivery formulation (enteric coating) or if the particles are to be loaded with a potentially toxic contrast agent (non-biodegradable coating).

The microspheres may be prepared by any means known in the art that is suitable for the preparation of particles containing poly[bis(trifluoroethoxy)phosphazene]. In a procedure according to an embodiment herein a "polymer solution" is prepared by mixing one or more polymer solvent(s) and the poly[bis(trifluoroethoxy)phosphazene and/or a derivative thereof until the polymer is dissolved.

Suitable solvents for use in the preparation of the polymer solution include any in which the polymer poly[bis(trifluoroethoxy)phosphazene and/or its derivatives are soluble. Exemplary solvents include, without limitation, ethyl-, propyl-, pentyl-, octylacetate, acetone, methylethylketone, methylpropylketone, methylisobutylketone, tetrahydrofurane, cyclohexanone, dimethylacetamide, acetonitrile, dimethyl ether, hexafluorobenzene or combinations thereof.

The polymer solution contains the poly[bis(trifluoroethoxy)phosphazene and/or its derivative polymer in a concentration of about 1% by weight of polymer to 20% by weight of polymer, preferably about 5% to 10% by weight of polymer. Other polymers, as discussed above, may be present in the solution, or may be added to the vessel in the form of a second solution powder or other form, if one wishes to include such polymers in the final particle.

In carrying out the process, the polymer solution is next dispensed, preferably in the form of drops or an aerosol, into a vessel containing a non-solvent. By "non-solvent" it is meant any organic or inorganic solvents that do not substantially dissolve the poly[bis(trifluoroethoxy)phosphazene polymer and which have a melting point that is lower relative to the melting point of the solvent in which the polymer is dissolved ("polymer solvent"), so that the non-solvent thaws before the solvent thaws in the course of the incubation step. Preferably, this difference between the melting point of the non-solvent and the polymer solvent is about 10° C., more preferably about 15° C., and most preferably, greater than about 20° C. Under certain conditions it has been found that the structural integrity of the resultant particle may be enhanced if the difference of the melting points of the polymer solvent and of the non-solvent is greater than 15° C. However, it is sufficient that the non-solvent point is merely slightly lower than that of the polymer solvent.

The non-solvent/polymer solvent combination is incubated for approximately 1 to 5 days or until the polymer solvent has been completely removed from the particles. While not wishing to be bound by theory, it is hypothesized that during the incubation, the non-solvent functions to extract the polymer solvent from the microscopic polymer solution droplets from the particles such that the polymer is at least gelled. As the incubation period passes, the droplets will shrink and the solvent becomes further extracted, leading to a hardened outer polymeric shell containing a gelled polymer core, and finally, after completion of the incubation, a complete removal of the residual solvent. To ensure that the polymeric droplets retain a substantially spherical shape during the incubation period, they are maintained in a frozen or substantially gelled state during most if not all of the incubation period. Therefore, the non-solvent temperature may stay below the melting point of the solvent during the cryoextraction process.

As shown in FIG. 1, at the vessel labeled (a), polymer solution droplets are shown being dispensed either with a syringe or other device at a controlled rate onto a top layer of liquid nitrogen. The nitrogen layer is situated over a bottom layer consisting of the selected non-solvent, which will eventually serve to extract the solvent from the frozen polymer solution droplets. The non-solvent layer has been previously frozen with liquid nitrogen prior to the dispensing of the polymer solution. The vessel labeled (b) shows the onset of the dewing of the frozen nonsolvent, into which the frozen polymeric droplets will sink. The vessel labeled (c) shows the cryoextraction procedure after approximately three days of incubation wherein the polymer solution droplets, incubated within the non-solvent, have been depleted of a substantial amount of solvent. The result is a gelled, polymeric particle in the form of a bead having a hardened outer shell. As can be seen by the representation, the non-solvent height within the vessel is slightly reduced due to some evaporation of the non-solvent. The size of the beads will shrink quite substantially during this process depending on the initial concentration of the polymer in the polymer solution.

Figure 2:
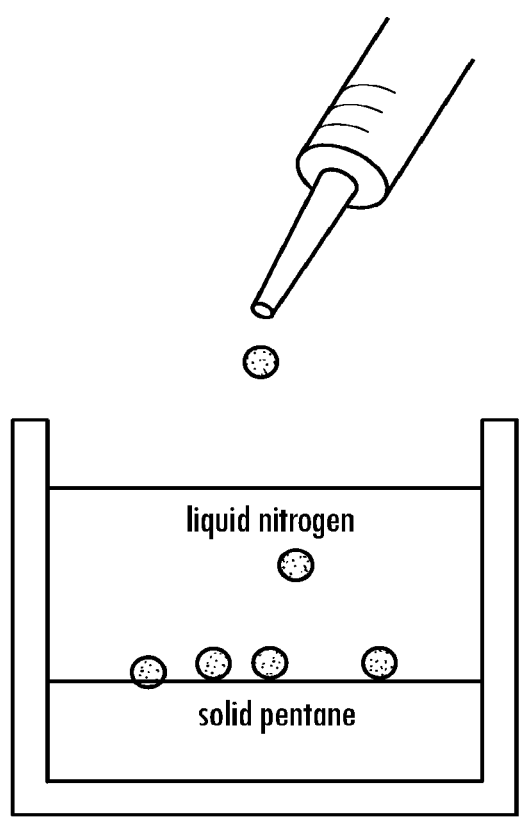
FIG. 2 shows the manual dripping technique by which the polymer solution was supplied to liquid nitrogen in preparation of the microspheres of Example 1, herein.

In one embodiment of a method of preparing a poly[bis(trifluoroethoxy)phosphazene-containing particle(s) according to the invention, such particles can be formed using any method known or to be developed in the art. Two exemplary preferred methods of accomplishing this include wherein (i) the non-solvent residing in the vessel in the method embodiment described above is cooled to close to its freezing point or to its freezing point prior to the addition of the polymer solution such that the polymer droplets freeze upon contact with the pre-cooled non-solvent; or (ii) the polymer droplets are frozen by contacting them with a liquefied gas such as nitrogen, which is placed over a bed of pre-frozen non-solvent (see, FIG. 2). In method (ii), after the nitrogen evaporates, the non-solvent slowly thaws and the microspheres in their frozen state will sink into the liquid, cold non-solvent where the extraction process (removal of the polymer solvent) will be carried out.

By modifying this general process, one may prepare particles that are hollow or substantially hollow or porous. For example, if the removal of the solvent from the bead is carried out quickly, for example, by applying a vacuum during the final stage of incubation, porous beads will result.

The particles of the invention can be prepared in any size desired, "Microspheres" may be obtained by nebulizing the polymer solution into a polymer aerosol using either pneumatic or ultrasonic nozzles, such as, for example a Sonotek 8700-60 ms or a Lechler US50 ultrasonic nozzle, each available from Sono[.tek] Corporation, Milton, N.Y., U.S.A. and Lechler GmbH, Metzingen, Germany. Larger particles may be obtained by dispensing the droplets into the non-solvent solution using a syringe or other drop-forming device. Moreover, as will be known to a person of skill in the art, the size of the particle may also be altered or modified by an increase or decrease of the initial concentration of the polymer in the polymer solution, as a higher concentration will lead to an increased sphere diameter.

In an alternative embodiment of the particles described herein, the particles can include a standard and/or a preferred core based on an acrylic polymer or copolymer with a shell of poly[bis(trifluoroethoxy)phosphazene. Such particles can provide a preferred spherical shape and improved specific gravity for use in a suspension of contrast media for embolization. The acrylic polymer based polymers with poly[bis(trifluoroethoxy)phosphazene shell described herein provide a substantially spherical shape, mechanical flexibility and compressibility, improved specific gravity properties. The core polymers may be formed using any acceptable technique known in the art, such as that described in B. Thanoo et al., "Preparation of Hydrogel Beads from Crosslinked Poly(Methyl Methacrylate) Microspheres by Alkaline Hydrolysis," J. Appl. P. Sci., Vol. 38, 1153-1161 (1990), incorporated herein by reference with respect thereto. Such acrylic-based polymers are preferably formed by polymerizing unhydrolyzed precursors, including, without limitation, methyl acrylate (MA), methyl methacrylate (MMA), ethylmethacrylate (EMA), hexamethyl (HMMA) or hydroxyethyl methacrylate (HEMA), and derivatives, variants or copolymers of such acrylic acid derivatives. Most preferred is MMA. The polymer should be present in the core in a hydrated or partially hydrated (hydrogel) form. Such polymers are preferably cross-linked in order to provide suitable hydrogel properties and structure, such as enhanced non-biodegradability, and to help retain the mechanical stability of the polymer structure by resisting dissolution by water.

Preferably, the core prepolymers are formed by dispersion polymerization that may be of the suspension or emulsion polymerization type. Emulsion polymerization results in substantially spherical particles of about 10 nm to about 10 microns. Suspension polymerization results in similar particles but of larger sizes of about 50 to about 1200 microns.

Suspension polymerization may be initiated with a thermal initiator, which may be solubilized in the aqueous or, more preferably, monomer phase. Suitable initiators for use in the monomer phase composition include benzoyl peroxide, lauroyl peroxide or other similar peroxide-based initiators known or to be developed in the art, with the most preferred initiator being lauroyl peroxide. The initiator is preferably present in an amount of about 0.1 to about 5 percent by weight based on the weight of the monomer, more preferably about 0.3 to about 1 percent by weight based on the weight of the monomer. As noted above, a cross-linking co-monomer is preferred for use in forming the hydrated polymer. Suitable cross-linking co-monomers for use with the acrylic-based principle monomer(s) used in preparing a polymerized particle core, include various glycol-based materials such as ethylene glycol dimethacrylate (EGDMA), diethylene glycol dimethacrylate (DEGDMA) or most preferably, triethylene glycol dimethacrylate (TEGMDA). A chain transfer agent may also be provided if desired. Any suitable MA polymerization chain transfer agent may be used. In the preferred embodiment herein, dodecylmercaptane may be used as a chain transfer agent in amounts acceptable for the particular polymerization reaction.

The aqueous phase composition preferably includes a surfactant/dispersant as well as a complexing agent, and an optional buffer. Surfactants/dispersants should be compatible with the monomers used herein, including Cyanamer® 370M, polyacrylic acid and partially hydrolyzed polyvinyl alcohol surfactants such as 4/88, 26/88, 40/88. A dispersant should be present in an amount of about 0.1 to about 5 percent by weight based on the amount of water in the dispersion, more preferably about 0.2 to about 1 percent by weight based on the amount of water in the dispersion. An optional buffer solution may be used if needed to maintain adequate pH. A preferred buffer solution includes sodium phosphates ($Na_2HPO_4$/$NaH_2PO_4$). A suitable complexing agent is ethylene diamine tetraacetic acid (EDTA), which may be added to the aqueous phase in a concentration of from about 10 to about 40 ppm EDTA, and more preferably about 20 to about 30 ppm. It is preferred that in the aqueous phase composition, the monomer to water ratio is about 1:4 to about 1:6.

The polymerization should take place at about ambient conditions, preferably from about 60° C. to about 80° C. with a time to gelation of about one to two hours. Stirring at rates of 100 to 500 rpm is preferred for particle formation, with lower rates applying to larger sized particles and higher rates applying to smaller sized particles.

Once PMMA (poly-MMA) particles, such as microparticles, are formed, they are preferably subjected to hydrolysis conditions typical of those in the art, including use of about 1-10 molar excess of potassium hydroxide per mol of PMMA. Such potassium hydroxide is provided in a concentration of about 1-15% potassium hydroxide in ethylene glycol. The solution is then heated preferably at temperatures of about 150-185° C. for several hours. Alternatively, to minimize reactant amounts and cost, it is preferred that lesser amounts of potassium hydroxide be used which are less than about 5 molar excess of potassium hydroxide per mole of PMMA, more preferably about 3 molar excess or less. For such hydrolytic reactions, a concentration of about 10-15% potassium hydroxide in ethylene glycol is also preferably used, and more preferably about 14% to about 15%. It will be understood by one skilled in the art, that heating conditions at higher temperatures may be used to decrease overall reaction times. Reaction times may be varied depending on the overall diameter of the resultant particles. For example, the following conditions are able to provide particles having about 35% compressibility and desired stability: for diameters of about 200-300 μm, the solution should be heated for about 7.5 to about 8.5 hours; for diameters of about 300-355 μm, about 9.5 to about 10.5 hours; for diameters of about 355-400 μm, about 11.5 to about 12.5 hours; and for about 400-455 μm, about 13.5 to about 14.5 hours, and the like. The particle size can be adjusted using variations in the polymerization process, for example, by varying the stirring speed and the ratio of the monomer to the aqueous phase. Further, smaller sizes can be achieved by increasing surfactant/dispersant ratio.

Following hydrolysis, particles are separated from the reaction mixture and their pH may be adjusted to any range as suited for further processing steps or intended uses. The pH of the particle core may be adjusted in from about 1.0 to about 9.4, preferably about 7.4 if intended for a physiological application. Since size, swelling ratio and elasticity of the hydrogel core material are dependent on pH value, the lower pH values may be used to have beneficial effects during drying to prevent particle agglomeration and/or structural damage. Particles are preferably sieved into different size fractions according to intended use. Drying of particles preferably occurs using any standard drying process, including use of an oven at a temperature of about 40°-80° C. for several hours up to about a day.

To provide desired surface properties to the hydrophilic hydrogel particles, in order to provide adhesion for receiving a poly[bis(trifluoroethoxy)phosphazene coating, the surface of the hydrogel may be subjected to treatment with any suitable ionic or non-ionic surfactant, such as tetraalkylammonium salts, polyalcohols and similar materials. A more permanent change in adhesion properties is brought about by rendering the surface of the particles hydrophobic by reaction of its polymethacrylic acid groups with a suitable reactant. Suitable reactants include, but are not limited to, hydrophobic alcohols, amides and carboxylic acid derivatives, more preferably they include halogenated alcohols such as trifluoroethanol. Such surface treatment also prevents delamination of the coating from the core once the coating is applied. Preferred surface treatments may include, without limitation, an initial treatment with thionyl chloride followed by reaction with trifluoroethanol. Alternatively, the surface may be treated by suspending the particles in a mixture of sulfuric acid and a hydrophobic alcohol, such as trifluoroethanol. Such treatments are preferred if the particles are to be coated in that they minimize any delamination of a coating.

Alternatively, in some preferred embodiments of the present invention, the PMA (poly-MA) core particles may be coated with a surface layer of and/or infused with barium sulfate. The barium sulfate is radio-opaque and aids in visualization of the finished particles when in use. It also provides enhanced fluidization properties to the particles such that it reduces agglomeration especially during drying and allows for fluid bed coating of the PMA particles with an outer coating of poly[bis(trifluoroethoxy)phosphazene, thereby providing improved adhesion between a poly[bis (trifluoroethoxy)phosphazene outer core and a polymeric acrylate core particles. By allowing fluidization even when the core particles are swollen, barium sulfate also improves the overall coating and adhesion properties. By enabling the coating of the core particles even in a swollen state with poly[bis(trifluoroethoxy)phosphazene, barium sulfate also reduces the potential tendency of the poly[bis(trifluoroethoxy)phosphazene shells to crack or rupture in comparison with coating the particles in a dry state and then later exposing the particles to a suspension in which the core particles swell and exert force on the shell of poly[bis (trifluoroethoxy)phosphazene. A coating of barium sulfate on the core particles is preferably applied by adhesion of the barium sulfate in the form of an opaque coating on the hydrogel surface of the PMA beads. Barium sulfate can further assist in reducing electrostatic effects that limit particle size. By allowing for absorption of additional humidity, the barium sulfate tends to counteract the electrostatic effects.

Barium sulfate crystals adhering only loosely to the PMA particles may be covalently crosslinked or chemically grafted to the particle surface by spraycoating a sufficient amount of an aminosilane adhesion promoter onto the PMA particle. This will help to effectively reduce barium sulfate particulate matter in solution after hydration of the particles. Exemplary particles include 3-aminopropyltrimethoxysilane and similar silane-based adhesion promoters, such as, for example, N-methyl-aza-2,2,4-trimethylsilacyclopentane, 2,2-dimethoxy-1,6-diaza-2-silacyclooctane, (3-trimethoxysilylpropyl)diethylene triamine, N-(3-(trimethoxysilyl)propyl)methanediamine, $N^1,N^2$-bis(3-(trimethoxysilyl)propyl) ethane-1,2-diamine, 1,3,5-tris(3-(trimethoxysilyl)propyl)-1, 3,5-triazinane-2-4-6-trione, and similar silane-based adhesion promoters.

In various embodiments of the present invention, polyphosphazene-coated microspheres may be provided with a hydrogel core containing various contrast agents suitable for enhanced visualization of such microspheres in vivo using magnetic resonance imaging (MRI), or derivative technologies thereof. Such contrast agents may include, but are not limited to, agents that include tantalum, gadolinium, samarium, and other agents that are known to the art. Examples of MRI contrast agents include, but are not limited to, ferric chloride, ferric ammonium citrate, gadolinium-DTPA (Gd-DTPA) with and without mannitol, Gd-DOTA, Gd-EDTA, $GdCl_3$, Gadodiamide, Gadoteridol, gadopentetate dimeglumine, Cr(III) agents, Mn(III)TPPS4 (manganese(III) tetra[4-sulfanatophenyl]porphyrin), Fe(III)TPPS4, manganese dichloride, Fe-EHPG (iron(III) ethylenebis-(2-hydroxyphenylglycine)), $^{99m}$Tc-iminodiacetate (Tc-IDA), chromium diethyl HIDA meglumine (Cr-HIDA), Gd-BOPTA (gadobenate dimeglumine), manganese(II)-dipyridoxal diphosphate (Mn-DPDP), gadolinium oxide, superparamagnetic iron oxides (SPIO, also "small particle iron oxides"), ultrasmall supermagnetic particle iron oxides (USPIO, also "ultrasmall particle iron oxides"), and the like. One aspect of the present invention affords a method of reducing the toxicity of various agents such as contrast agents like Fe(III)TPPS4, by containing the agent within the hydrogel core of the microspheres disclosed herein.

In various embodiments of the present invention, polyphosphazene-coated microspheres may be provided with a hydrogel core containing rare earth compounds with paramagnetic qualities suitable for enhanced visualization of such microspheres in vivo using magnetic resonance imaging, paramagnetic transition methods, or derivative technologies thereof known in the art.

Constituent atoms or molecules of paramagnetic materials have permanent magnetic moments (dipoles), even in the absence of an applied field. This generally occurs due to the presence of unpaired electrons in the atomic/molecular electron orbitals. In pure paramagnetism, the dipoles do not interact with one another and are randomly oriented in the absence of an external field due to thermal agitation, resulting in zero net magnetic moment. When a magnetic field is applied, the dipoles will tend to align with the applied field, resulting in a net magnetic moment in the direction of the applied field. In the classical description, this alignment can be understood to occur due to a torque being provided on the magnetic moments by an applied field, which tries to align the dipoles parallel to the applied field. However, the truer origins of the alignment can only be understood via the quantum-mechanical properties of spin and angular momentum.

If there is sufficient energy exchange between neighboring dipoles they will interact, and may spontaneously align or anti-align and form magnetic domains, resulting in ferromagnetism (permanent magnets) or antiferromagnetism, respectively. In general, paramagnetic effects are quite small: the magnetic susceptibility is of the order of $10^{-3}$ to $10^{-5}$ for most paramagnets, but may be as high as $10^{-1}$ for synthetic paramagnets such as ferrofluids.

For low levels of magnetization, the magnetization of paramagnetic rare earth compounds is approximated by Curie's law:

$$M=C(B/T)$$

where:
M is the resulting magnetization,
B is the magnetic flux density of the applied field, measured in tesla,
T is absolute temperature, measured in Kelvin,
C is a material-specific Curie constant.

Curie's law indicates that the susceptibility of paramagnetic materials is inversely proportional to their temperature. However, Curie's law is only valid under conditions of low magnetization, since it does not consider the saturation of magnetization that occurs when the atomic dipoles are all aligned in parallel (after everything is aligned, increasing the external field will not increase the total magnetization since there can be no further alignment).

A further alternative for improving visualization of microparticles made as noted herein include the absorption of a water soluble organic dye inside the hydrogel core particles. Exemplary dyes are preferably those FDA dyes approved for human use and which are known or to be developed for safe, non-toxic use in the body and which are capable of providing acceptable contrast. Organic dyes may include dyes such as D&C Violet no. 2 and others preferably approved for medical device uses, such as for contact lenses and resorbable sutures. Whereas barium sulfate operates as an inorganic filler and finely dispersed pigment that makes the particles visible by light diffraction due to small crystal size, the dyes when impregnated in the particles absorb the complementary part of the visible color spectrum.

Particles, including microparticles made in accordance with the foregoing process for forming a core hydrogel polymer are then coated with poly[bis(trifluoroethoxy)phosphazene and/or its derivatives. Any suitable coating process may be used, including solvent fluidized bed and/or spraying techniques. However, preferred results may be achieved using fluidized bed techniques in which the particles pass through an air stream and are coated through spraying while they spin within the air stream. The poly[bis(trifluoroethoxy)phosphazene or derivative polymer is provided in dilute solution for spraying to avoid clogging of the nozzle.

Exemplary solvents for use in such solutions include ethyl acetate, acetone, hexafluorbenzene, methyl ethyl ketone and similar solvents and mixtures and combinations thereof, most preferred is ethyl acetate alone or in combination with isoamyl acetate. Typical preferred concentrations include about 0.01 to about 0.3 weight percent poly[bis(trifluoroethoxy)phosphazene or its derivative in solution, more preferably about 0.02 to 0.2 weight percent poly[bis(trifluoroethoxy)phosphazene, and most preferably about 0.075 to about 0.2 weight percent. It should be understood based on this disclosure that the type of hydrogel core can be varied as can the technique for coating a particle, however it is preferred that a core which is useful in the treatment techniques and applications described herein is formed and subsequently coated with poly[bis(trifluoroethoxy) phosphazene and/or its derivatives as described herein.

As previously discussed, the particles can be used in various medical and therapeutic applications, such as embolization, drug delivery, imaging (ultrasound) and as tracer particles. For example, in one embodiment, the invention includes a method of minimizing blood flow to a specific tissue in a mammal. This process, commonly referred to as embolization, includes occluding or obstructing at least a portion of a vessel, or the entire vessel, with one or more of the particles of the invention. Such procedure is particularly useful in the treatment of diseases and pathologies that involve undesirable vascularized tissues, for example, tumor tissue or disorders involving the uncontrolled proliferation of certain cells such as endometriosis. In such procedures, the particle(s) are prepared in accordance with the procedures described above, and may be inserted into the blood vessel by any invasive or non-invasive medical practice known or to be developed in the art such as via a catheter, a syringe, or a surgical incision. The embolization can be carried out such that only a portion of the blood vessel is occluded, or the entire vessel may be occluded. In the method, if desired, one may use particles that have been loaded with an active agent, such as a cytostatic agent, an anti-inflammatory agent, an anti-mitogenic or cell proliferation active agent, a hormone, or any other desirable active agent, as described herein. Embolization particles according to the present invention are capable of demonstrating improved optical visibility, additional radiopacity, and an optimum specific density of about 1.17 $g/cm^3$. The embolization particles in this invention may be used with different dyes as markers as noted above for particle sizes, embedded pharmaceuticals for localized drug delivery and controlled drug elution characteristics.

For use in embolization therapy, particle density is preferably taken into consideration to ensure beneficial properties for particle delivery. Possible clogging of a catheter-based delivery system may occur if using a density-mismatched delivery medium. In addition, it is desirable to include a certain minimum amount of contrast agent in the delivery medium to achieve sufficient levels of fluoroscopic contrast during surgery. Currently, the polymethacrylate hydrogel density is between 1.05 $g/cm^3$ and 1.10 $g/cm^3$ depending on the equilibrium water content. The most common iodinated nonionic contrast agent media with 300 mg iodine per ml have densities of 1.32-1.34 $g/cm^3$. As used herein, "buoyancy" refers to the ability of the particles to be substantially free floating in solution that occurs when the density of the particle is substantially the same as the medium in which it is suspended. Coated particles formed in accordance with the present invention as described herein can reach buoyancy when there is approximately 30% contrast agent in the delivery medium, however, such levels can be adjusted for such preferred use according to techniques described herein.

One method for increasing the density of the particles is by use of heavy water or deuterium oxide ($D_2O$). When heavy water is used to swell the particles, $D_2O$ displaces $H_2O$, thereby increasing the weight of the particles for better dispersion and buoyancy levels. Typically this leads to the ability to add higher amounts of contrast agent of at least about 5% using such a technique. However, some equilibrating effect can occur over time when the particles are contacted with an aqueous solution of contrasting agent. Thus, it is preferred that when using $D_2O$ for this purpose, either that suspension times are kept to a minimum or, more preferably, that the contrast agent be provided in a solution which also uses $D_2O$.

Alternatively, particles of pH 1 can be neutralized with cesium hydroxide and/or the final neutralized particles can be equilibrated with cesium chloride. Such compounds diffuse cesium into the particles, such that either the cesium salt of polymethacrylic acid is formed or polymethacrylic acid is diffused and thereby enriched with cesium chloride.

The cesium increases the density of the particles, thereby increasing the ability to add higher amounts of contrast agent. Typical buoyancy levels can be adjusted using the cesium technique such that about 45 to about 50% contrast agent may be added to the delivery medium as is desired for embolization. Cesium salts are non-toxic and render the particles visible using fluoroscopy. Cesium's atomic weight of 132.9 g/mol is slightly higher than that of iodine providing beneficial effects including increase in overall density and enhancement of X-ray contrast visibility even without a contrast agent. For certain cancer treatments where a radioactive isotope of cesium is desired, such active agent can be used as an alternative cesium source rendering the particles buoyant in an embolic solution as well as able to be used as an active treatment source.

The above-noted techniques for improving density of particles, such as microparticles for embolization or other applications where density and/or buoyancy in solution are applicable properties may be applied in to the preferred particles described herein and/or may be applied for other similar particles. It should be understood that the disclosure is not limited to cesium and/or $D_2O$ treatment of the preferred particles herein and that such techniques may have broader implications in other particles such as other acrylic-based hydrogels and other polymeric particles.

As noted above, barium sulfate may be used between the core particles and the preferred poly[bis(trifluoroethoxy) phosphazene coating or introduced into the interior of the core particles using any technique known or to be developed in the art. Also, organic dyes may similarly be included in the particle core. These materials, particularly the barium sulfate, also contribute to an increase in density as well as providing radiopacity. In addition to a general density increase as provided by the above-noted $D_2O$ or cesium compounds, the barium sulfate allows this benefit even upon substantial and/or full hydration, allowing particles in suspension to remain isotonic. Thus, a barium sulfate powder coating can provide an inert precipitate having no effect on physiological osmolarity.

In yet other exemplary embodiments of the present invention, contrast agents for conventional radiographic imaging with radio-opaque agents such as cesium, iodine, or ionic or nonionic iodine-containing compounds may be provided either within the hydrogel core or injected as a suspension liquid with the microspheres. Examples of iodine contrast agents include both ionic and non-ionic agents, including, but not limited to, Diatrizoate, Metrizoate, Ioxaglate, Iopamidol, Iohexol, Ioxilan, Iopromide, Iodixanol, Ioxitalamin, and the like. Generally, the term "radio-opaque" agent refers to any substance or agent which blocks, absorbs, scatters, or reflects any radiation outside the visible light spectrum, including, but not limited to, X-rays (in the wavelength range of 0.01 to 10 nm), beta rays (having, for example, velocities of about 35,000 to 180,000 miles per second), gamma rays (having an energy in the range of $10^4$ to $10^7$ eV), radiation used in radiation therapy (for example, therapy to treat cancer), and other harmful radiation (such as that resulting from nuclear disasters and nuclear weapons). Suitable radio-opaque agents include, but are not limited to, those comprising platinum, gold, silver, bismuth, mercury, lead, barium, calcium, zinc, aluminum, iron, gallium, iodine, tungsten, and any combination thereof. Other suitable radio-opaque agents include, but are not limited to, those commercially available as radio-opaque agents for medical uses, such as ionic and nonionic intravenous radiocontrast agents, diagnostic barium and gastrographin preparations, and gallium preparations. In one embodiment, the radio-opaque agent blocks, absorbs, scatters, or reflects any radiation outside the visible light spectrum, including, but not limited to, X-rays, beta rays, and gamma rays, which are emitted from radioisotopes, such as those used in the medical industry (for example, in radiation therapy and medical diagnostic testing). Examples of radioisotopes in clinical use include, but are not limited to, radioisotopes of gallium (for example, $^{67}Ga$ or $^{68}Ga$), iodine (for example, $^{123}I$, $^{126}I$, $^{131}I$, $^{132}I$, or $^{133}I$), indium (for example, $^{111}In$ or $^{113}In$), thallium (for example, $^{201}Tl$ or $^{203}Tl$), as well as $^3H$, $^{11}C$, $^{14}C$, $^{13}N$, $^{18}F$, $^{22}Na$, $^{24}Na$, $^{31}Si$, $^{32}P$, $^{35}S$, $^{36}Cl$, $^{38}Cl$, $^{42}K$, $^{45}Ca$, $^{51}Cr$, $^{52}Mn$, $^{54}Mn$, $^{55}Fe$, $^{59}Fe$, $^{60}Co$, $^{63}Zn$, $^{65}Zn$, $^{68}Zn$, $^{82}Br$, $^{85}K$, $^{85}Kr$, $^{89}Sr$, $^{99}Tc$, $^{99m}Tc$, $^{99m}Re$, $^{101}Re$, $^{105}Re$, $^{121m}Te$, $^{122m}Te$, $^{125m}Re$, $^{137}Cs$, $^{165}Tm$, $^{167}Tm$, $^{168}Tm$, $^{81m}Kr$, $^{33}Xe$, $^{90}Y$, $^{213}Bi$, $^{77}Br$, $^{18}F$, $^{95}Ru$, $^{97}Ru$, $^{103}Ru$, $^{105}Ru$, $^{107}Hg$, $^{203}Hg$, $^{182}Ta$, $^{192}Ir$, $^{198}Au$, and the like.

It should be understood, based on this disclosure, that the various buoyancy additives noted above can be used independently or in combination to provide the most beneficial effects for a given core particle and coating combination.

The invention also includes methods of delivering an active agent to a localized area within the body of a mammal. The method includes contacting the localized area with at least one of the particles of the invention as described above, such that an effective amount of the active agent is released locally to the area. As used herein, "contact" or "contacting" the localized area with at least one particle is intended to include situating at least one particle and an active agent in sufficiently close proximity to the intended area such that the desired effect is achieved. In this example an effective amount of the active agent is exposed to the localized area. Diseases or pathologies that may be treated by this method include any wherein the localized or topical application of the active agent achieves some benefit in contrast to the systemic absorption of the drug. Suitable active agents include NSAIDS, steroids, hormones, nucleic acids, agents used in the treatment of disorders of the gastrointestinal tract, such as, ulcers, Crohn's disease, ulcerative colitis, and irritable bowel syndrome. Other active agents may include tacrolimus, sirolimus, paclitaxel, cis-/carboplatins, antineoplastic agents, doxorubicine and/or receptor blocking agents, for example, $\alpha v\beta 3$ integrin blockers, which inhibit cell attachment.

If the particle formulated for delivery of an active agent to a localized area is about 1 to about 1,000 µm in diameter, the drug loaded microspheres can be applied to localized areas within the mammalian body using syringes and/or catheters as a delivery device, without causing inadvertent occlusions. For example, using a contrast agent, a catheter can be inserted into the groin artery and its movement monitored until it has reached the area where the localized administration is desired. A dispersion of the particles in a suitable injection medium can be injected through the catheter, guaranteeing only a specific area of the body will be subjected to treatment with drug loaded beads (particles). As will be understood to a person of skill in the art, injection mediums include any pharmaceutically acceptable mediums that are known or to be developed in the art, such as, for example, saline, PBS or any other suitable physiological medium. In accordance with a further embodiment described herein, the invention includes an injectible dispersion including particles and a contrasting agent which particles are substantially dispersed in the solution. In a preferred embodiment, the particles are also detectible through fluoroscopy.

The polymeric particles of the invention may be used to prepare a sustained release formulation of an active agent for oral administration. The formulation comprises a particle, as described above, loaded with an active agent. The polymeric particle utilized may be hollow, substantially hollow or solid. The particle can be loaded with the active agent either by dispersion or solvation of the active agent in the polymer solution prior to the production of micro-sized particles through spray droplets, pastillation of a polymer melt or carrying out of a cryoextraction process. Alternatively, an unloaded polymer particle can be prepared and subsequently immersed in solutions containing active agents. The particles are then incubated in these solutions for a sufficient amount of time for the active agent to diffuse into the matrix of the polymer. After drying the particles, the active agent will be retained in the polymer particle. If this loading mechanism is utilized, drug loading can be controlled by adjusting drug concentrations of the incubation medium and removing the particles from the incubation medium when an equilibrium condition has been attained.

Moreover, it is envisioned that the active agent can be selected so as to complement the action of the particles in a synergistic fashion, especially if the particles are being used in an occlusive or embolization procedure. For example, if the tissue to which one wishes to minimize blood flow is a tumor tissue, one may wish to load the particles used in the occlusion with a cytostatic drug, antiangiogenic agents, or an antimitotic drug.

Also provided is a method of tracing the passage of a particle through a blood vessel or other cavity in a mammalian body. The method includes injecting into the vessel, cavity, or a conduit adjacent to such cavity or vessel, at least one particle, wherein the particle is at least a particle prepared in accordance with the procedures described above, and wherein the particle further comprises a component to allow its location to be detected visually, electronically, or by other imaging means.

In a medical setting, a contrast agent is any substance that is used to enhance the visibility of structures or fluids within the body. In exemplary embodiments of the present invention, the particles may include a contrast agent that may aid in the visualization of the particle as it passes through the body cavity, blood vessel, and/or other locale. In general, in this application smaller particles are preferred, such as those in the range of about 1 to about 10 μm, especially if the particles are to be injected into the bloodstream. However, the particles may be of any size so long as, for this purpose, they are not large enough to occlude the blood vessel, body cavity, or adjacent cavity or vessel to which the procedure is being applied.

In various preferred embodiments of the present invention, contrast agents may be provided within particles of the invention as described herein. In other preferred embodiments of the present invention, contrast agents may be delivered along with particles of the invention as a suspension or delivery medium. In yet other preferred embodiments of the present invention, contrast agents may be delivered in a separate injection or instillation than the particles of the invention.

If the particles are loaded with a contrast agent, their movement can be visualized with X-ray machines, or any other imaging modality, depending on the contrast agent utilized. However, if the particles do not contain a contrast agent, the flow of the particles may be visualized using $^{19}$F-NMR based computer tomography.

If desired, one may coat particles containing a contrast agent with a polymer coating. The polymer coating may comprise any polymer known or to be developed in the art, including any phosphazene polymers. In a preferred embodiment of the present invention, the polymer coating for particles is poly[bis(trifluoroethoxy) phosphazene or a derivative thereof. If there is any toxicity or concern of toxicity with respect to the contrast agent, it is desirable that the one or more coating is non-biodegradable. Depending on the nature of the visualization procedure, such contrast agents may be provided (for example, from the class of conventional radiographic contrast enhancing agents such as ionic or nonionic iodine-containing compounds (Imeron™, Optiray™, etc.).

In conventional or x-ray based radiography, contrast agents may be either positive or negative, Positive contrast agents have a higher attenuation density than the surrounding tissue. This means that the contrast agent looks more opaque than the surrounding tissue when seen on an x-ray. Negative contrast media has a lower attenuation density than the surrounding tissue. This means that the contrast looks less opaque than the body. Negative contrast is only found as a gas. Positive contrast agents are substances with high atomic numbers, that are also non-toxic.

Positive contrast agents which may be used in some embodiments of the present invention include, but are not limited to, agents comprising barium, cesium, iodine, gadolinium, tantalum, and compounds or compositions containing these elements. Negative contrast agents occur as non-toxic gases, including but not limited to, air, oxygen, carbon dioxide, nitrogen, helium, argon, xenon, and mixtures thereof.

Contrast agents for Magnetic Resonance Imaging (MRI) are commonly used in diagnostic imaging. These agents improve the resolution of MRI images by increasing the brightness in various parts of the body where the agent resides. Most contrast agents that have been approved for human use are extracellular. Where magnetic resonance imaging (MRI) is employed for visualization of particles of the present invention, the contrast agent to be provided may be chosen from the class of rare earth compounds, such as gadolinium-, tantalum-, and samarium-chelates and other compounds and compositions, as is known to the art. Gadolinium (and other lanthanide)-based agents are heavier and better able to absorb high-energy X-rays than iodine. Gadolinium-based contrast agents have a relatively short residence time in the vascular system.

More recently, intracellular agents have been introduced that have longer residence times and allow extended imaging procedures without the need for repeated injections of the agent.

Extracellular fluid (ECF) agents include products such as Magnevist, Prohance, and Omniscan. These agents are generally nonionic and a recent report, points out that the development of nonionic contrast agents for MRI has paralleled that for iodinated contrast materials. Ionic chelates are also hyperosmolar and some of their side effects may be attributed to this property. Gadodiamide (Omniscan®, Winthrop Pharm.) is a nonionic complex with 40% osmolality of Gd-DTPA. It has a median lethal dose of 34 mmol/kg resulting in a safety ratio of 2-3 times that of Gd-DOTA, and 3-4 times that of Gd-DTPA. No abnormal serum bilirubin levels occur; however, elevated serum iron levels have been reported in some patients. The efficacy of this contrast is similar to that of Gd-DTPA. Gadoteridol (Prohance®, Squibb) is the third intravenous contrast agent on the market. It is a low osmolar, nonionic contrast, as is Gadodiamide. Indications for use and efficacy are similar to the other agents.

Three types of intravascular contrast agents have been developed: Gd-DTPA labeled albumin, Gd-DTPA labeled dextran, and chromium-labeled red blood cells. Intravascular contrast agents normally remain confined to the intravascular space, compared to Gd-DTPA which distributes throughout the extracellular fluid space. This is a result of intravascular agents having a molecular weight of approximately 70,000 and above, compared to a molecular weight of 590 for Gd-DTPA. There are several advantages of intravascular agents. They can assess perfusion in areas of ischemia and provide information about capillary permeability in areas of reperfusion. They can show the extent of tumor neovascularity and associated permeability changes. Finally, they are useful in studies requiring prolonged imaging.

Since the hydrogel core component in embodiments of the present invention may be derived from an anionic hydrogel polymer, such as polymethacrylic acid and the like, the incorporation of multivalent metal compounds, including aforementioned rare earth or other metals, may facilitate a favorable ionic interaction of these compounds, such as by ionic crosslinking or similar ionic interaction, thus providing for favorable retention or accumulation of these compounds in the particles and hence providing for a sustained release effect of such compounds in various embodiments according to the present invention.

Yet another class of contrast agents are Ultrasmall Supermagnetic Iron Oxide Particles (USPIOs). small particles of ferrite used as paramagnetic contrast medium in MR imaging. These agents exhibit strong T1 relaxation properties, and due to susceptibility differences to their surroundings also produce a strongly varying local magnetic field, which enhances T2 relaxation to darken the contrast media-containing structures. As particulate matter they are taken up by the reticuloendothelial system. Very small particles of less than 300 μm also remain intravascular for a prolonged period of time and thus can serve as blood pool agents. The agents are also known by the abbreviation SPIOs ("small particle iron oxides" or "superparamagnetic iron oxides") and USPIOs ("ultrasmall particle iron oxides" or "ultrasmall superparamagnetic iron oxides"). SPIOs have been used as darkening contrast agents for liver imaging and for darkening the bowel.

In yet other alternate preferred embodiments of the present invention, the particles may comprise radioisotopes or radionuclides as tracer agents. Such radioisotopes may be localized and identified visually using conventional or computerized scintillation or beta/gamma camera technology. Using image fusion or co-registration techniques, scintillation images can be superimposed on images from modalities such as CT or MRI to highlight the anatomic region of the body in which the radiopharmaceutical is concentrated. Most diagnostic radionuclides used in medical imaging emit gamma rays, while the cell-damaging properties of beta particles may be used in therapeutic applications. Common radioisotopes used in embodiments of the present invention include, but are not limited to, technetium-99m, iodine-123 and -131, thallium-201, gallium-67, fluorine-18, and indium-111. However, any radioisotope in clinical use may be used in embodiments of the present invention, including but are not limited to, any radioisotope of gallium (for example, $^{67}$Ga or $^{68}$Ga), iodine (for example, $^{123}$I, $^{126}$I, $^{131}$I, $^{132}$I, or $^{133}$I), indium (for example, $^{111}$In or $^{113}$In), thallium (for example, $^{201}$Tl or $^{203}$Tl), as well as $^{3}$H, $^{11}$C, $^{14}$C, $^{13}$N, $^{18}$F, $^{22}$Na, $^{24}$Na, $^{31}$Si, $^{32}$P, $^{35}$S, $^{36}$Cl, $^{38}$Cl, $^{42}$K, $^{45}$Ca, $^{51}$Cr, $^{52}$Mn, $^{54}$Mn, $^{55}$Fe, $^{59}$Fe, $^{60}$Co, $^{63}$Zn, $^{65}$Zn, $^{68}$Zn, $^{82}$Br, $^{85}$K, $^{85}$Kr, $^{89}$Sr, $^{99}$Tc, $^{99m}$Tc, $^{99m}$Re, $^{101}$Re, $^{105}$Re, $^{121m}$Te, $^{122m}$Te, $^{125m}$Re, $^{137}$Cs, $^{165}$Tm, $^{167}$Tm, $^{168}$Tm, $^{81m}$Kr, $^{33}$Xe, $^{90}$Y, $^{213}$Bi, $^{77}$Br, $^{18}$F, $^{95}$Ru, $^{97}$Ru, $^{103}$Ru, $^{105}$Ru, $^{107}$Hg, $^{203}$Hg, $^{182}$Ta, $^{192}$Ir, $^{198}$Au, and the like.

The invention also includes the method of carrying out an enhanced ultrasound imaging procedure (sonography). In order to do this, one administers to the ultrasound subject at least one hollow microcapsule to the area of the ultrasound subject that one wishes to visualize. Such administration can be accomplished by any means known or to be developed in the art, including by use of a syringe, catheter or other invasive or non-invasive medical device, and/or by a surgical incision. In such method, it is preferable to use particles which are hollow or substantially hollow, i.e. having a gas-filled inner cavity that is equal to at least about 20%, at least about 30%, at least about 40%, at least about 50%, at least about 80%, at least about 90%, of the volume of the entire particle. The hollow particles are administered to a portion of the ultrasound subject which one wishes to image. Such particles enhance the ultrasound image by increasing the echogenicity resulting from use of diagnostic ultrasound modalities due to their abrupt density change, when compared to the surrounding tissue. The hollow cavities of the particles act to reflect the ultrasound, thereby enhancing the image.

In still other embodiments of the present invention, inclusion of gas-filled microbubbles provide improved visualization of microspheres in tissue when used in contrast-enhanced ultrasound (CEUS). CEUS is the application of ultrasound contrast agents to traditional medical sonography. Microbubbles have a high degree of echogenicity, which is the ability of an object to reflect the ultrasound waves. The echogenicity difference between the gas in the microbubbles and the soft tissue surroundings of the body is immense. Thus, ultrasonic imaging using microbubble contrast agents enhances the ultrasound backscatter, or reflection of the ultrasound waves, to produce a unique sonogram with increased contrast due to the high echogenicity difference. Contrast-enhanced ultrasound can be used to image blood perfusion in organs, measure blood flow rate in the heart and other organs, and has other applications as well.

Coating material selection for particles containing microbubbles determines how easily the particle is taken up by the immune system. A more hydrophilic material tends to be taken up more easily, which reduces the microbubble residence time in the circulation. This reduces the time available for contrast imaging. The microbubble's shell material also affects microbubble mechanical elasticity. The more elastic the material, the more acoustic energy it can withstand before bursting The gas content of microbubbles in particles of the present invention is important when employed for ultrasound contrast because the gas selection largely determines echogenicity. When gas bubbles are caught in an ultrasonic frequency field, they compress, oscillate, and reflect a characteristic echo—this generates the strong and unique sonogram in contrast-enhanced ultrasound. Gas cores can be composed of air, or heavy gases like perfluorocarbon, or nitrogen. Heavy gases are less water-soluble so they are less likely to leak out from the microbubble to impair echogenicity Therefore, microbubbles with heavy gas cores are likely to last longer in circulation Targeting ligands that bind to receptors characteristic of intravascular diseases can be conjugated to microbubbles, enabling the microbubble complex to accumulate selectively in areas of interest, such as diseased or abnormal tissues. This form of molecular imaging, known as targeted contrast-enhanced ultrasound, will only generate a strong ultrasound signal if targeted microbubbles bind in the area of interest. Targeted contrast-enhanced ultrasound can potentially have many applications in both medical diagnostics and medical therapeutics.

The present invention is further illustrated by the following examples, which are not to be construed in any way as imposing limitations upon the scope thereof. On the contrary, it is to be clearly understood that resort can be had to various other aspects, embodiments, modifications, and equivalents thereof which, after reading the description herein, can suggest themselves to one of ordinary skill in the art without departing from the spirit of the present invention or the scope of the appended claims.

Further, it is to be understood that this invention is not limited to specific materials, agents, polyphosphazenes, or other compounds used and disclosed in the invention described herein, including in the following examples, as each of these can vary. It is also to be understood that the terminology used herein is for the purpose of describing particular aspects or embodiments and is not intended to be limiting. Should the usage or terminology used in any reference that is incorporated by reference conflict with the usage or terminology used in this disclosure, the usage and terminology of this disclosure controls.

Unless indicated otherwise, temperature is reported in degrees Centigrade and pressure is at or near atmospheric. An example of the preparation of a polyphosphazene of this invention is provided with the synthesis of poly[bis(trifluoroethoxy)phosphazene] (PzF) polymer, which may be prepared according to U.S. Patent Application Publication No. 2003/0157142, the entirety of which is hereby incorporated by reference.

Also unless indicated otherwise, when a range of any type is disclosed or claimed, for example a range of molecular weights, layer thicknesses, concentrations, temperatures, and the like, it is intended to disclose or claim individually each possible number that such a range could reasonably encompass, including any sub-ranges encompassed therein. For example, when the Applicants disclose or claim a chemical moiety having a certain number of atoms, for example carbon atoms, Applicants' intent is to disclose or claim individually every possible number that such a range could encompass, consistent with the disclosure herein. Thus, by the disclosure that an alkyl substituent or group can have from 1 to 20 carbon atoms, Applicants intent is to recite that the alkyl group have 1, 2, 3, 4, 5, 6, 7, 8, 9, 10, 11, 12, 13, 14, 15, 16, 17, 18, 19, or 20 carbon atoms. In another example, by the disclosure that microspheres have a diameter of approximately 500 to 600 µm, Applicants include within this disclosure the recitation that the microspheres have a diameter of approximately 500 µm, approximately 510 µm, approximately 520 µm, approximately 530 µm, approximately 540 µm, approximately 550 µm, approximately 560 µm, approximately 570 µm, approximately 580 µm, approximately 590 µm, and/or approximately 600 µm, including any range or sub-range encompassed therein. Accordingly, Applicants reserve the right to proviso out or exclude any individual members of such a group, including any sub-ranges or combinations of sub-ranges within the group, that can be claimed according to a range or in any similar manner, if for any reason Applicants choose to claim less than the full measure of the disclosure, for example, to account for a reference that Applicants are unaware of at the time of the filing of the application.

EXAMPLE 1

Microspheres having a diameter of approximately 500 to 600 µm were prepared. First, a polymer solution was prepared by dissolving poly[bis(trifluoroethoxy) phosphazene polymer of a molecular weight $3 \times 10^6$ g/mol in the polymer solvent ethyl acetate to obtain a 2% (wt/v) polymer solution. Four milliliters of this polymer solution was manually dripped into liquid nitrogen using a 5 ml syringe. This dispersion was dispensed onto a frozen layer of 150 milliliters of pentane. (See FIG. 2.) The cryoextraction was allowed to proceed for three days. Subsequently, polymeric particles were retrieved from the reaction vessel, and were air dried at 21° C.

EXAMPLE 2

Microspheres having a diameter of approximately 350 to 450 µm were prepared. First, a polymer solution was prepared by dissolving poly[bis(trifluoroethoxy)phosphazene polymer of a molecular weight $3 \times 10^6$ g/mol in ethyl acetate to obtain a 1% (wt/v) polymer solution. Four milliliters of this polymer solution was manually dripped into liquid nitrogen using a 5 ml syringe. This dispersion was dispensed onto a frozen layer of 150 milliliters of pentane. (See FIG. 2.) The cryoextraction was allowed to proceed for three days. Subsequently, polymeric particles were retrieved from the reaction vessel and were air dried at 21° C.

EXAMPLE 3

Microspheres having a diameter of approximately 500 to 600 µm were prepared. First, a polymer solution was prepared by dissolving poly[bis(trifluoroethoxy) phosphazene polymer of a molecular weight $12 \times 10^6$ g/mol in methylisobutylketone to obtain a 2% (wt/v) polymer solution. Four milliliters of this polymer solution was manually dripped into liquid nitrogen using a 5 ml syringe. This dispersion was dispensed onto a frozen layer of 150 milliliters of a 1:9 (v/v) ethanol/pentane mixture (See FIG. 2.). The cryoextraction was allowed to proceed for three days. Subsequently, polymeric particles were retrieved from the reaction vessel, and dried under reduced pressure at 21° C.

EXAMPLE 4

Microspheres having a diameter of approximately 500 to 600 µm were prepared. First, a polymer solution was prepared by dissolving poly[bis(trifluoroethoxy)phosphazene polymer of a molecular weight $9 \times 10^6$ g/mol in isoamylketone to obtain a 2% (wt/v) polymer solution. Four milliliters of this polymer solution was manually dripped into liquid nitrogen using a 5 ml syringe. This dispersion was dispensed onto a frozen layer of 150 milliliters of pentane. (See FIG. 2.) The cryoextraction was allowed to proceed for three days. Subsequently, polymeric polymers were retrieved from the reaction vessel and dried under reduced pressure at 21° C.

EXAMPLE 5

Microspheres having a diameter of approximately 500 to 600 µm were prepared. First, a polymer solution was prepared by dissolving poly[bis(trifluoroethoxy)phosphazene polymer of a molecular weight $16 \times 10^6$ g/mol in cyclohexanone to obtain a 2% (wt/v) polymer solution, Four milliliters of this polymer solution was manually dropped into liquid nitrogen using a 5 ml syringe. This dispersion was dispensed onto a frozen layer of 150 milliliters of a 1:1 (v/v) ethanol/diethyl ether mixture. (See FIG. 2.) The cryoextraction was allowed to proceed for three days. Subsequently, polymeric particles were retrieved from the reaction vessel and dried under reduced pressure at 21° C.

EXAMPLE 6

Microspheres having a diameter of approximately 500 to 600 µm were prepared. First, a polymer solution was prepared by dissolving poly[bis(trifluoroethoxy)phosphazene polymer of a molecular weight $3 \times 10^6$ g/mol in ethyl acetate to obtain a 2% (wt/v) polymer solution. Four milliliters of this polymer solution was manually dripped into liquid nitrogen using a 5 ml syringe. This dispersion was dispensed onto a frozen layer of 150 milliliters of hexane. (See FIG. 2.) The cryoextraction was allowed to proceed for three days. Subsequently, polymeric particles were retrieved from the reaction vessel and air dried at 21° C.

EXAMPLE 7

Microspheres having a diameter of approximately 500 to 600 µm were prepared. First, a polymer solution was prepared by dissolving poly[bis(trifluoroethoxy)phosphazene polymer of a molecular weight 3×10⁶ g/mol in ethyl acetate to obtain a 2% (wt/v) polymer solution. Four milliliters of this polymer solution was manually dripped into liquid nitrogen using a 5 ml syringe. This dispersion was dispensed onto a frozen layer of 150 milliliters of ethanol. (See FIG. 2.) The cryoextraction was allowed to proceed for three days. Subsequently, polymeric particles were retrieved from the reaction vessel and air dried at 21° C. The particles were noticeably gel-like and after drying were ellipsoid in shape.

EXAMPLE 8

Microspheres having a diameter of approximately 500 to 600 μm were prepared. First, a polymer solution was prepared by dissolving poly[bis(trifluoroethoxy)phosphazene polymer of a molecular weight 3×10⁶ g/mol in ethyl acetate to obtain a 2% (wt/v) polymer solution. Four milliliters of this polymer solution was manually dripped into liquid nitrogen using a 5 ml syringe. This dispersion was dispensed onto a frozen layer of 150 milliliters of diethylether. (See FIG. 2.) The cryoextraction was allowed to proceed for three days. Subsequently, polymeric particles were retrieved from the reaction vessel and air dried at 21° C. The resultant particles were, after drying, compact and uniformly spherical.

EXAMPLE 9

Figures 6, 7:
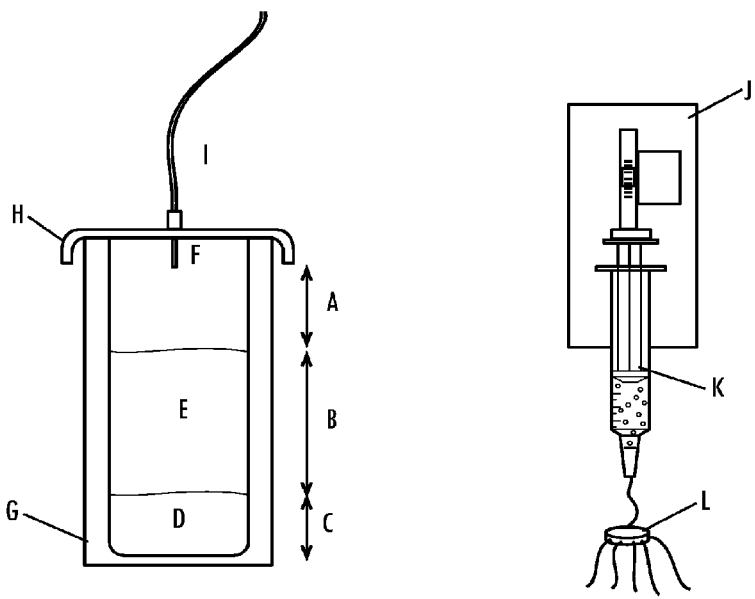

A two liter cryovessel as shown in FIG. 6 was filled with 100 milliliters of diethyl ether as a non-solvent. Liquid nitrogen was slowly added until the non-solvent froze. The vessel was then filled with additional liquid nitrogen, until the amount of liquid nitrogen rose approximately 5 to 10 cm when measured vertically above the non-solvent layer. The vessel was closed with an insulated lid, and a syringe needle connected via Teflon tubing to a syringe pump was inserted through a small opening in the lid.

The syringe pump as shown in FIG. 7, was used to dispense between 5 to 15 milliliters of the 5 to 40 mg/ml polymer solution in ethyl acetate, slowly into the cryovessel. The rate of the pump was adjusted to approximately 10 milliliters dispensing volume per hour. A Teflon® cylinder with one inlet and one to eight outlets is used to distribute the dispensed volumes into several vessels in parallel. (It is preferable that the ratio of solvent to non-solvent volume stays below 10% (v/v). Otherwise the particles may adhere to one another.) After the polymer solution was completely dispensed into the vessel, another 100 milliliters of non-solvent was slowly poured on top of the liquid nitrogen.

In carrying out this process, it is noted that it is preferable that the needle tips used for dispensing are small, such as the G33 size. Additionally, the dropping distance should be more than 5 cm, so that the droplets aided by gravity immediately sink into the liquid nitrogen upon hitting the surface.

The liquid nitrogen in the vessel was slowly allowed to evaporate, taking approximately one day. The non-solvent slowly began to melt, and the polymer solution droplets, still frozen, sank into the cold non-solvent. After another day of incubation, the now gelled polymer beads (particles) were retrieved from the vessel by simple filtration. They were allowed to dry at room temperature for approximately 30 minutes and then were ready for use in any of the applications described herein.

EXAMPLE 10

Figure 3A:
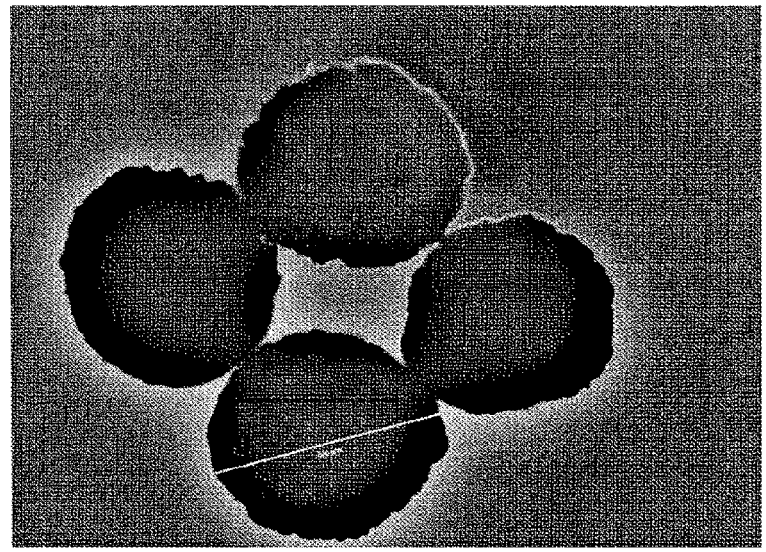
FIG. 3A and FIG. 3B show unloaded polyphosphazene particles (microspheres) as prepared by one embodiment of the cryoextraction method as described herein.
Figure 3B:
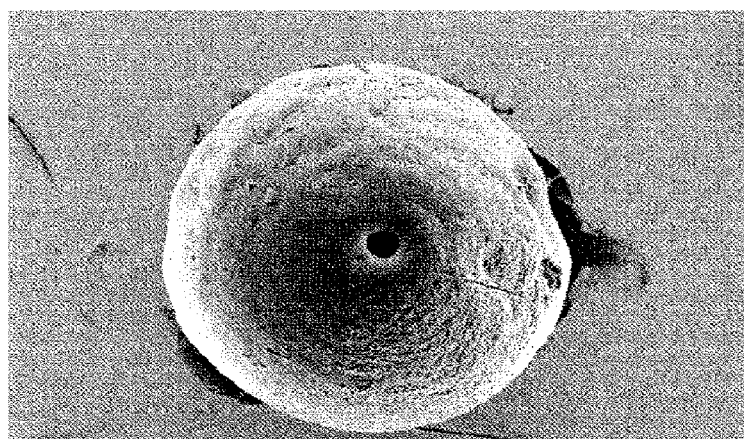

The microspheres prepared by the process of Example 1 were examined for shape and surface morphology by optical microscope, scanning electron microscope (SEM) and atomic force microscopy. The results of these analyses are shown in FIGS. 3A and 3B). FIG. 3A shows the microspheres as they appear using an optical microscope at 4× magnification. FIG. 3B shows a microsphere as it appears using a scanning electron microscope at 100× magnification.

It can be seen that surface morphology of the unloaded spheres is typical for semi-crystalline polymers above glass transition temperature. Amorphous as well crystalline regions are prevalent throughout the sample surface. The surface is macroporous in nature, with pore sizes ranging from nanometers to few micrometers in diameter.

Figure 4A:
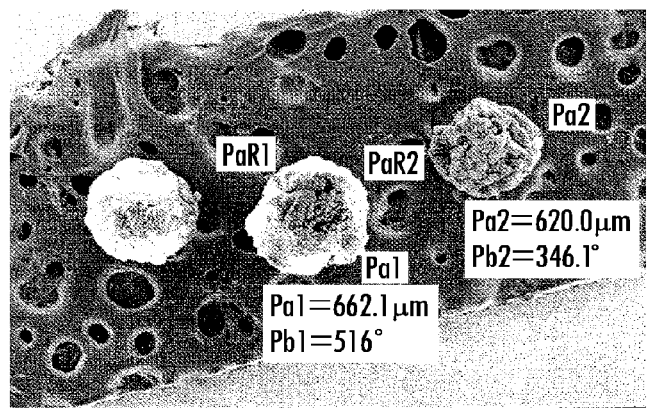
FIG. 4A and FIG. 4B show particles (microsphere) formed according to one embodiment of the invention loaded with bovine insulin (20% (wt/wt)) at 100× magnification SEM.
Figure 4B:
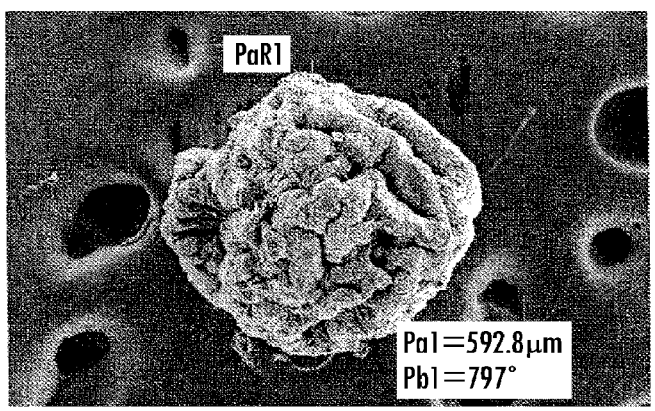
Figure 5A:
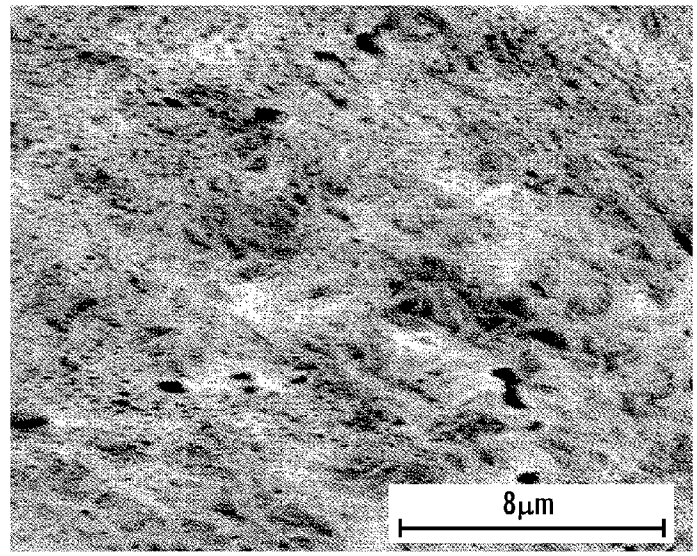
FIG. 5A and FIG. 5B show the surface morphology of unloaded polyphosphazene microspheres.
Figure 5B:
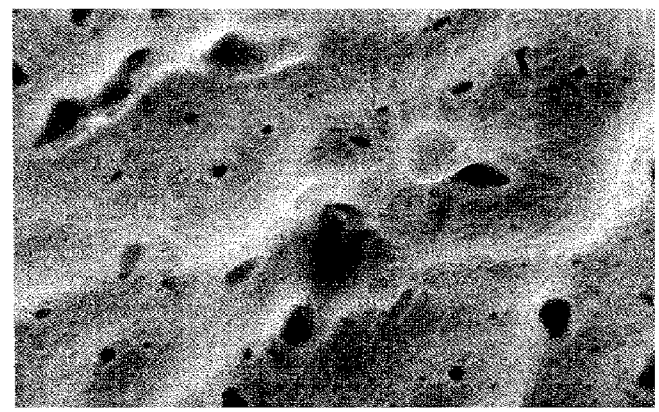

Particles loaded with bovine insulin were also analyzed using scanning electron microscopy (100× magnification). The result of these analyses can be seen in FIG. 4A and FIG. 4B).

EXAMPLE 11

Several polymerizations were carried out using varying combinations of PMMA and three different crosslinking monomers (EDGMA, DEGDMA and TEGDMA), different radical initiators (benzoyl peroxide (BPO) and lauroyl peroxide (LPO), EDTA as a complexing agent and varying dispersants (Cyanamer 370M, polyacrylic acid (PAA) and varying types of polyvinyl alcohol (PVA) to achieve the preferred core particles. In some polymerizations, sodium phosphate buffer solution ($Na_2HPO_4/NaH_2PO_4$) was used. It was observed that some of the reaction procedures went unsuccessful due to the type of dispersant and concentration chosen. Failure of the dispersant was demonstrated in the form of early onset of an exothermic reaction, coalescing aqueous and organic phases and premature onset of the vitrification phase. Only the successful runs are shown in Table 1, which includes the components, concentrations, and reaction conditions for such samples (1-6).

TABLE 1

| | | Sample | | | | | |
|---|---|---|---|---|---|---|---|
| | | 1 | 2 | 3 | 4 | 5 | 6 |
| Monomer | | PMMA | PMMA | PMMA | PMMA | PMMA | PMMA |
| | | 99.0 g | 190.0 g | 182.0 g | 200.2 g | 200.2 g | 200.2 g |
| Crosslinker | | EGDMA | EGDMA | EGDMA | DEGDMA | TEGDMA | TEGDMA |
| | | (1 wt %/ monomer) | (1 wt %/ monomer) | (1 wt %/ monomer) | (0.5 mol %/ monomer) | (0.5 mol %/ monomer) | (0.5 mol %/ monomer 7.5 mMol DDM) |
| Radical Initiator | | LPO (0.3 wt % monomer) | LPO (0.3 wt % monomer) | LPO (0.3 wt % monomer) | LPO (0.3 wt % monomer) | LPO (0.3 wt % monomer) | LPO (0.3 wt % monomer) |

TABLE 1-continued

| | Sample | | | | | |
|---|---|---|---|---|---|---|
| | 1 | 2 | 3 | 4 | 5 | 6 |
| Complexing Agent | EDTA 22 mg | EDTA 44 mg | EDTA 44 mg | EDTA 56 mg | EDTA 56 mg | EDTA 56 mg |
| Monomer/Water Ratio | 1:5 | 1:5 | 1:5 | 1:6 | 1:6 | 1:6 |
| Dispersant | PVA 4/88 35% PVA 26/88 65% 1 wt %/water | PVA 4/88 35% PVA 26/88 65% 0.5 wt %/water | PVA 26/88 0.25 wt %/water | PVA 26/88 0.23 wt %/water | PVA 26/88 0.23 wt %/water | PVA 26/88 0.23 wt %/water |
| Buffer Solution | No | No | No | Yes | Yes | Yes |
| Reaction Temperature/Time | 1 h 67° C. 2 h 70° C. 1 h 80° C. | 1 h 67° C. 2 h 70° C. 1 h 80° C. | 1 h 67° C. 2 h 70° C. 1 h 80° C. | 1 h 67° C. 2 h 70° C. 1 h 80° C. | 1 h 67° C. 2 h 70° C. 1 h 80° C. | 1 h 67° C. 2 h 70° C. 1 h 80° C. |
| Outcome (particle size) | 1-50 μm due to dispersant conc. | 20-200 μm due to dispersant conc. | 100-200 μm due to dispersant conc. | 1-100 μm due to initial stirring at 400 rpm | 1-100 μm due to initial stirring at 400 rpm | 50-1,000 μm due to initial stirring at 130 rpm |

EXAMPLE 12

Hydrogel microparticles formed in accordance with the procedures described herein were evaluated for buoyancy and suspension properties for use in embolization applications. The microparticles included a sample using unmodified polymethacrylic acid potassium salt hydrogel particles (Sample A); a sample using trifluoroethyl esterified polymethacrylic acid potassium salt hydrogels (Sample B); and a sample using the same hydrogel as Sample B, but wherein the particles were coated with poly[bis(trifluoroethoxy)phosphazene (Sample C). An isotonic phosphate buffered saline solution of pH 7.4 having 0.05 volume % Tween™ 20 was prepared by dissolving 5 phosphate buffered saline tablets (Fluka®) in 999.5 ml of milliQ ultrapure water. 0.5 ml of Tween 20™ surfactant was added to the solution. Solutions having between 20 and 50 percent by volume of Imeron300® contrast agent in the isotonic buffered saline solution were then prepared for evaluation.

The contrast agent solutions which were prepared were then placed in 4 ml vials in aliquots of 2 ml each. To the vials, 50-80 mg of the hydrated hydrogel Samples A-C were added. Each Sample was first hydrated by adding to 100 mg of dry hydrogel microparticles either 900 mg of isotonic phosphate buffered saline solution or $D_2O$ to obtain 1 ml swollen hydrogel. Buoyancy properties were measured immediately and every 10 minutes thereafter until buoyancy equilibrium was achieved and/or surpassed.

All of the particles reached equilibrium density in the contrast agent solution having 30-40% contrasting agent within 5 min. Particles which were swollen with $D_2O$ were heavier within the first 10 minutes, but the $D_2O$ did diffuse out of the particles over time within 15-20 min. of immersion. If additional water which could displace the $D_2O$ were not added, microparticles hydrated with $D_2O$ would be able to increase the contrast agent percentage achievable with adequate buoyancy by as much as 5%. Particles began to float to the top over time when the contrast agent was added in percentages of 40%-50%.

The equilibrium buoyancy (matching densities) was achieved for Sample C in 31±1 volume percent of contrast agent in solution. With regard to Samples A and B, swelling behavior and subsequent density are typically dependent on crosslinking content, pH, ionic strength and valence of cations used. However, it was assumed herein that the swelling does not influence buoyancy due to the sponge-like nature of the polymethacrylic acid hydrogel material. After such material was coated with the poly[bis(trifluoroethoxy)phosphazene as in Sample C, a time lag of swelling was observed and buoyancy equilibrium was slower to achieve.

EXAMPLE 13

In order to take account of the time lag and to achieve a more preferred density, as well as to enhance the fluoroscopic visibility of the particles, cesium treatment was then effected for the types of microparticles used in Samples B and C of Example 12.

100 mg of Sample C and of Sample B were hydrated each for 10 min. in a 30 weight percent solution of sodium chloride. The supernatant liquid was decanted after equilibrium and the microparticles were washed thoroughly with deionized water. They were then equilibrated for another 10 min., decanted and suspended in 3 ml of surfactant-free isotonic phosphate buffer solution at a pH 7.4. The effect on buoyancy was then evaluated using contrast agent solutions varying from 20 to 50% by volume of Imeron® 300. In this Example, 0.1 g of the microparticles of Samples B and C were used. 3.5 ml of Imeron 300 contrast agent were provided to the initial buffer solution which included 4.0 ml isotonic phosphate buffer/Tween™ 20 solution.

The equilibration procedure using cesium chloride yielded particles of increased density. Both microparticle samples showed a final buoyancy in the Imeron® 300 contrast agent solutions at concentrations of 45-50% contrast agent, regardless of the presence or absence of Tween™ 20 surfactant. The conditions for saturation appeared to be dependent upon the initial pH of the particles, the pH used during the procedure and the corresponding saturation with methacrylic acid groups in the particle. At pH below 3.6, constant exchange between protons and cations was observed. As a result, more beneficial results were shown at pH above about 3.6 and below about 6.6 to temper the amount of cesium. Within the preferred range, buoyancy can be varied. At reasonably neutral levels, based on test at pH of 7.4, the microparticles did not lose their buoyancy after storage in the contrast agent buffered solution over night.

EXAMPLE 14

Figure 8:
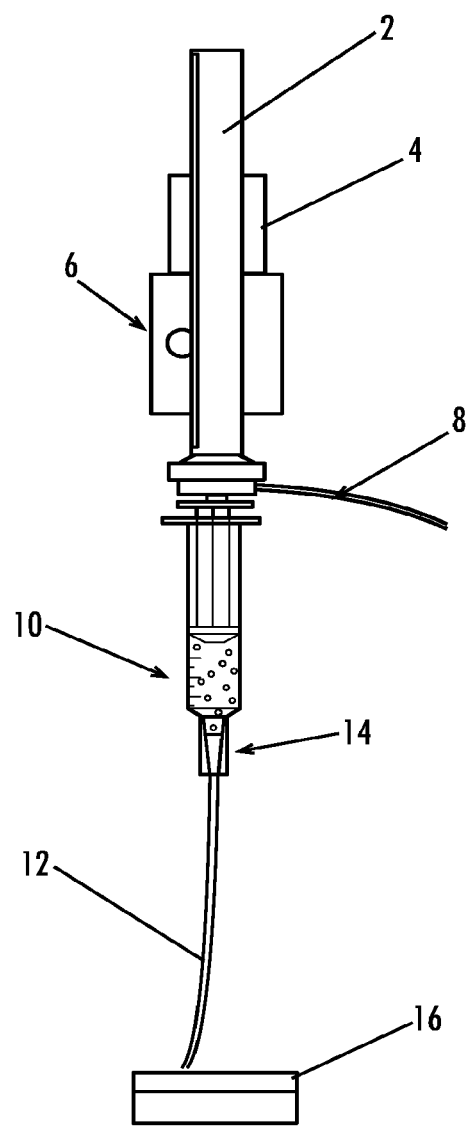
FIG. 8 is a cross-sectional view of an apparatus for use in microcatheter testing of microparticles in Example 14 herein.

Further compressibility and mechanical property testing were done on microspheres in accordance of Samples B and/or C of Example 12. A pressure test stand which was used for further evaluation is shown in FIG. 8. An automated syringe plunger 2 having a motor 4 for providing a variable feed rate of 0 to 250 mm/h and a gear box 6 was further equipped with a Lorenz pressure transducer 8 capable of measuring forces in the 0 to 500 N range. The syringe plunger 2 was in communication with a syringe body 10 as shown. The digital output of the transducer was recorded using a personal computer. The syringe body 10 was filled with 5 ml of a solution of contrast agent in isotonic phosphate buffer/surfactant (Tween™ 20) solution in a concentration of about 30-32 volume percent contrast agent. Microparticles were provided to the syringe as well in an amount of 56 mg dry mass. The syringe contents were then injected through the microcatheter 12 which was attached to the distal end 14 of the syringe. The microcatheter had a lumen diameter of 533 µm. The force needed to push the microparticles through the catheter into the Petri dish 16 (shown for receiving microparticle solution) was measured and recorded as pressure.

In order to make certain calculations, the following information was applied as based on typical use of microspheres for embolization. Typically such microspheres have a water content of about 90% such that a vial for embolization would therefore contain 0.2 mg of embolization particles in 9.8 ml of injection liquid (2 ml of hydrated microparticles in 8 ml supernatant liquid). Standard preparation procedures include adding 8 ml of Imeron® 300 contrast agent to the contents of a single vial. This would provide an equilibrium concentration of contrast agent of 8 ml/(9.8 ml+8 ml)=44.9 volume percent within an injection solution. The solution is typically drawn up in 1 ml syringes for final delivery. The injection density thus equals:

$$\rho = V_{Emb}/V_{Tot} = 2 \text{ ml}/18 \text{ ml} = 0.111 \text{ Embolization agent per volume fraction.}$$

The Sample C spheres demonstrated approximately the same equilibrium water content as typical embolization spheres. To achieve the same injection density desired for typical surgical procedures, 56 mg of Sample C microspheres were added to 5 ml of a 31 volume percent contrast agent solution in isotonic phosphate buffer and surfactant as noted above.

The Sample B and C microspheres were evaluated in different microcatheters of equal lumen diameter at a pH of 7.4. Injections in both the horizontal and vertical direction were made under different buoyancy levels and using different swelling levels (based on pH of 6.0 in contrast to pH 7.4). The results demonstrated that as long as the diameter of the microspheres was below the internal diameter of the microcatheter, the microparticles passed through the catheter without additional frictional force in the same manner as the reference solution. An increase to about 1.0 to 1.4 kg gravitation force was measured when the microparticle diameter reached the same dimension as the lumen diameter. At roughly 20% compression, forces of about 1.5-2.3 kg were needed to overcome frictional forces within the catheter. Forces greater than 5 kg were taken as a guideline for moderate to high injection pressures. When particles are heavier than the injection medium, clogging was observed when injecting in the vertical position. When injecting the microparticles in the horizontal position, it was observed that serious clogging was alleviated and that larger volumes were injectible over time.

Injection pressure was further minimized when a lower pH (reduced swelling) was used in combination with horizontal injection such that the injection pressures were comparable to the injection media itself. In addition, injection of Sample C microparticles also exhibited a good injection pressure pattern at a physiological pH. The catheter entrance did not clog and each peak in the curve corresponded to either a single microparticle or number of particles passing through the catheter.

The results of the various catheter simulation tests shows that the invention can be used to form injectible microparticles having a density which substantially matches the density of the injection medium for embolization use. The particles' compressibility can further be such that it can be injected without forces over more than about 5 kg on the syringe plunger. The pH of the injection medium can be taken down to about 6 or injections can be done horizontally to increase the ease of passage of Sample B and C microparticles through the catheter. Once within the blood stream, the particles can expand to their original size in the pH 7.4 environment.

Additional swelling tests were conducted on the microparticles of Sample C and it was observed that when ion concentrations were low, swelling increased. In higher concentrated solutions, swelling decreased. Continued dilution of the microparticles of Sample C in a buffer solution led to an increase from 17% to 20% in size of the microparticles. When mixed into an isotonic phosphate buffer solution, the microparticles initially increase in size between 83.8 and 97%, wherein in deionized water, size increases are from about 116.2 to about 136.6%, referring to the dry particles.

In further testing to evaluate the compressibility of the microparticles of Sample C, the syringe pressure test stand of FIG. 8 was used, however, an optical microscope was used to evaluate the microparticles as they passed through a progressively narrowed pipette which was attached to polyethylene tubing connected to the syringe containing a phosphate buffer solution suspension of microparticles of Sample C. The pipette narrowed to an inner diameter of 490 µm and the pipette was mounted to a Petri dish such that the narrowest part was submerged in phosphate buffer solution to avoid optical distortion and to collect the liquid ejected from the pipette during measurement. Optical microscope pictures were taken of the microparticles passing through the pipette before and during compression. In observing the microparticles, none of them underwent a fracture, nor did they form debris or coating delamination after passing through the narrow site. Microparticles which were chosen to be deliberately too big for the narrow site (for a compression of about 40%) did not break or rupture, but clogged the narrow site instead. The maximum compressibility under a reasonable amount of force on the microparticles while still allowing the microparticles to pass through the catheter was about 38.7%. Based on these evaluations, the microparticles according to Sample C demonstrate properties that would allow particles which are too large to clog the catheter rather than break up and cause potential damage to the patient. The test results provided suggested preferred use parameters for Sample C microparticles for embolization use as shown in Table 2 below:

TABLE 2

| Particle Radius s (μm) | Constriction (μm) | Compression (%) | Force Needed (kg) |
| --- | --- | --- | --- |
| 340 | 540 | 25.9 and 26.5 | 2.58 and 1.92 |
| 360 | 540 | 33.3 | 3.19 |
| 330 | 540 | 22.2 | 2.83 |
| 330 | 540 | 22.2 | 2.14 |
| 370 | 540 | 37.0 and 37.3 | 3.59 and 2.77 |
| 330 | 540 | 22.2 | 2.08 |
| 320 | 540 | 18.5 and 18.4 | 1.61 and 1.38 |
| 330 | 540 | 22.2 | 1.71 |

Figure 9A:
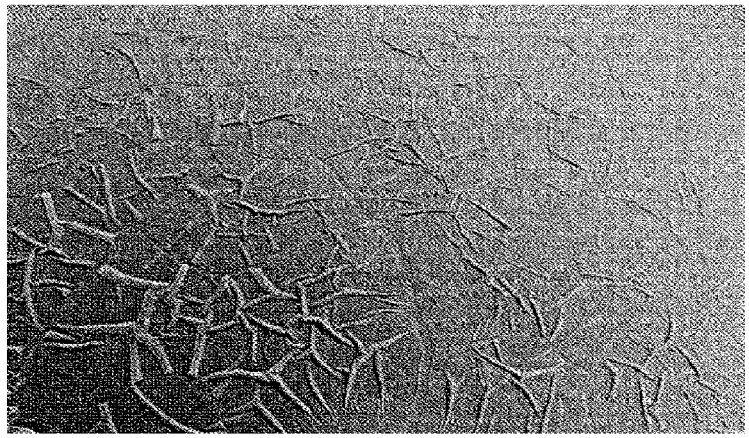
FIGS. 9A and 9B show an SEM at 1.0K× magnification of the surface of the Sample C microparticles just after the hydration/dehydration cycle and at a 50.00K× magnification of the film thickness of microparticles formed in accordance with Sample C of Example 12 used in the evaluation of Example 14, respectively.
Figure 9B:
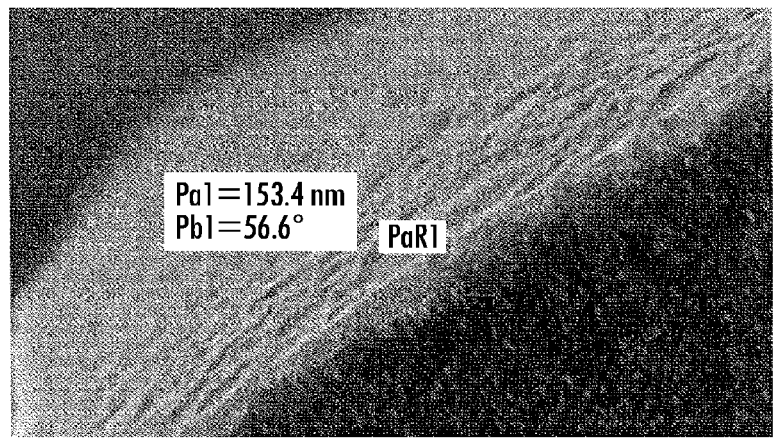
Figure 10A:
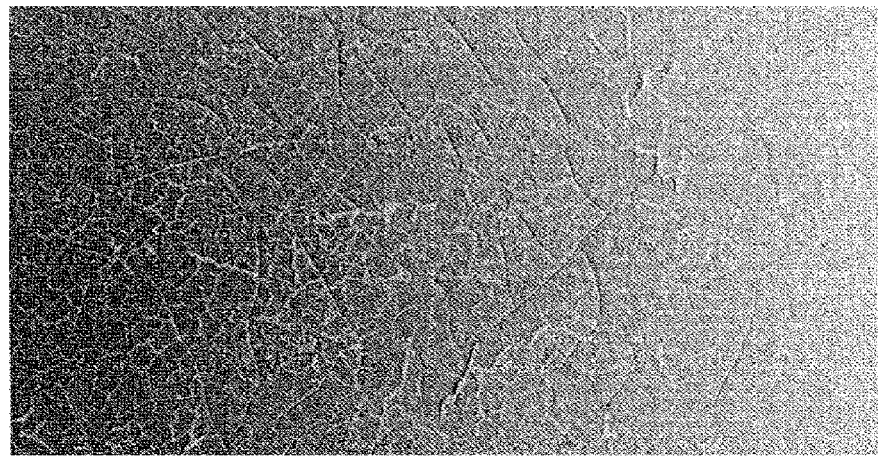
FIGS. 10A, 10B, 10C and 10D are SEMs of microparticles made in accordance with Sample C of Example 12 used in the evaluation of Example 14 after passing through a catheter showing surface features (FIGS. 10A, 10B and 10C) at 1.0K× magnification and at 5.0K× magnification (FIG. 10D)
Figure 10B:
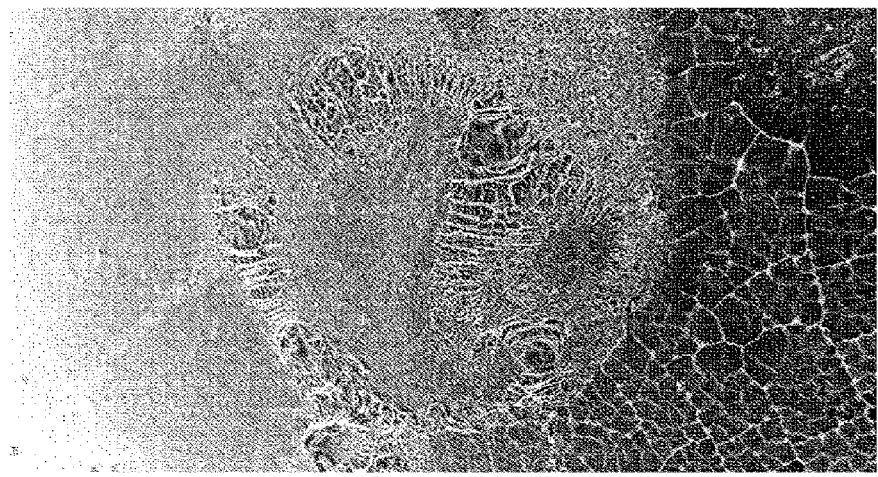
Figure 10C:
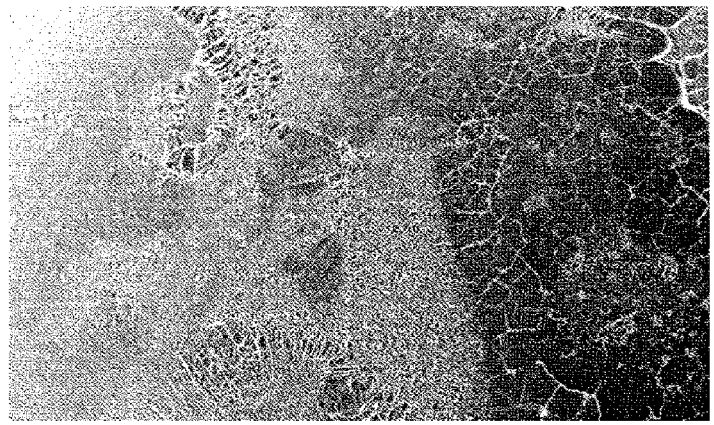
Figure 10D:
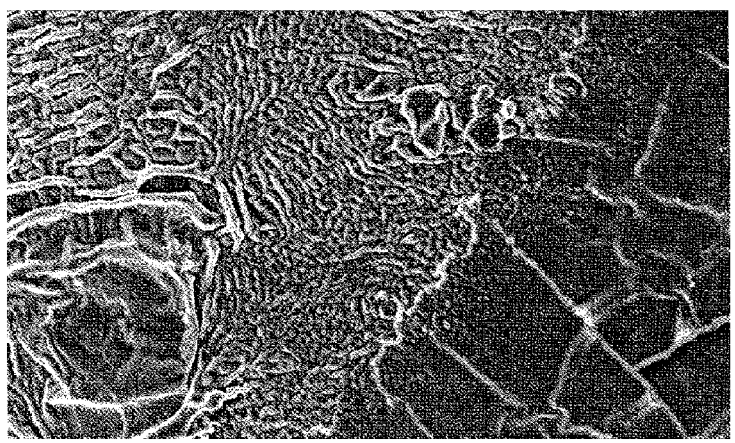

Sample C microparticles were further subjected to mechanical and thermal stress stability testing. Microparticles, after passing through a Terumo Progreat Tracker catheter were washed with deionized water to remove residual buffer solution along with contrast agent. They were dehydrated for 12 h at 60° C. and then transferred to an SEM for surface analysis. They were compared with particles from the original batch of microparticles which had undergone the same hydration/dehydration cycle in milliQ ultrapure water, but which had not been passed through the catheter. FIGS. 9A and 9B show the surface of the Sample C microparticles just after the hydration/dehydration cycle and the film thickness of an exemplary Sample C microparticle, respectively. SEMs after passing through a catheter at various magnifications (FIGS. 10A, 10B, 10C and 10D) show that the coating did not delaminate (FIG. 10A). Some microparticles did demonstrate some stretching out in the coating film (FIGS. 10B and 10C). However, a closer magnification as in FIG. 10D demonstrates that the morphology of the coating layer is still intact.

Figure 11A:
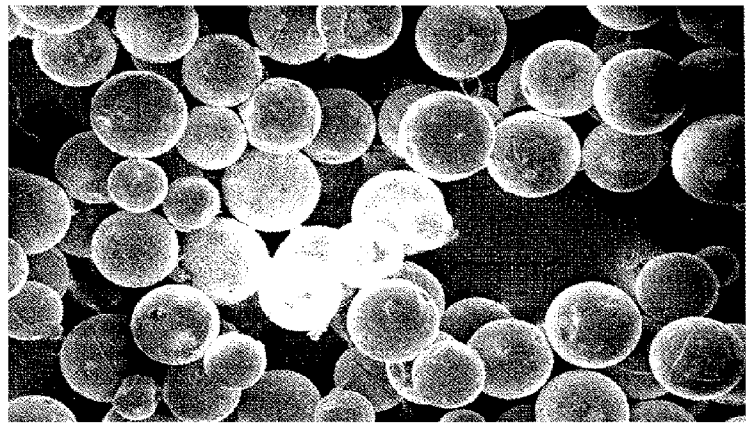
FIGS. 11A, 11B, 11C and 11D are SEMs of microparticles formed in accordance with Sample C of Example 12 after thermal stress testing in Example 14.
Figure 11B:
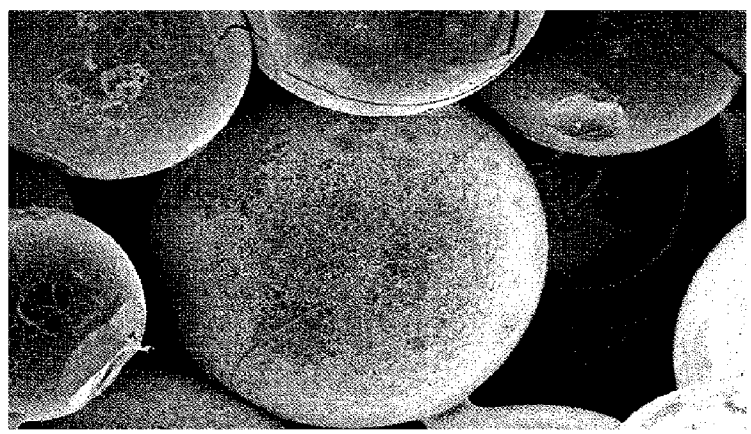
Figure 11C:
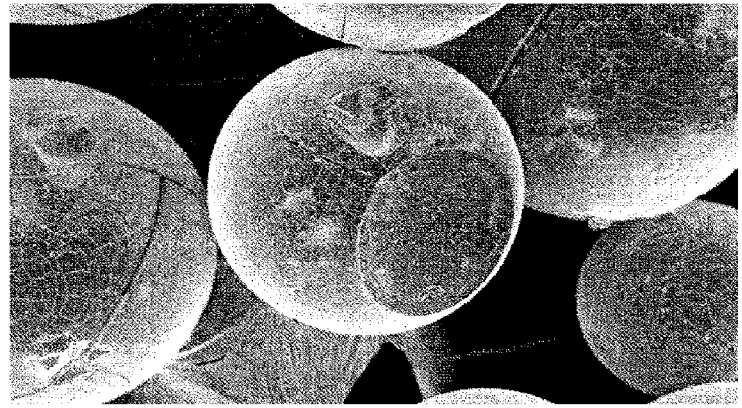
Figure 11D:
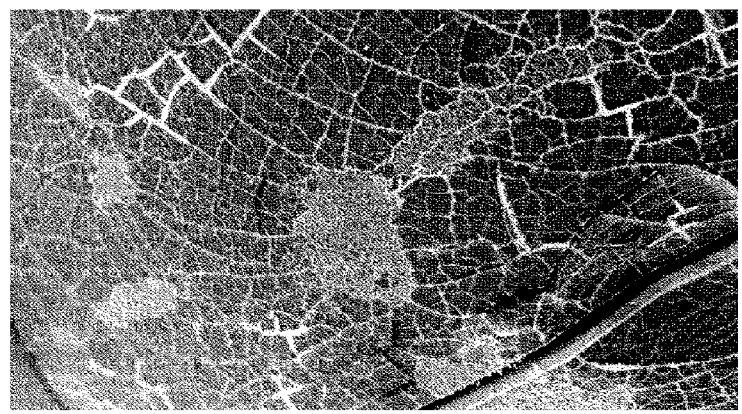

A sterilizer was filled with 2 l of deionized water and 10 vials each having 56 mg of Sample C microparticles in 3.3 g of solution of isotonic phosphate buffer/surfactant (Tween™ 20) and turned on. The water boiling point was reached about 15 min. after the start of the sterilizer, and temperature was held at that point for 3 min. to remove air by water vapor. The vessel was then sealed shut to raise pressure and temperature to 125° C. and 1.2 bar pressure. This took approximately 10 min. The temperature was then maintained for 15 min, and then the vessel was shut down for a cooling phase. A temperature of 60° C. was reached about 30 min later, after which the vessel was vented, the samples withdrawn and the vessel shut tightly. A sample vial was opened, and the supernatant liquid decanted. The microparticles were washed with deionized water. After dehydration, they were subjected to measurement using an SEM. The results demonstrated only a small number of delaminated coatings on the microparticles under such thermal stress (see FIG. 11A in the strong white contrast portion). The overall percentage of such microparticles was only about 5 to 10%. Close up, the film delamination which did occur appears to have occurred along crystalline-amorphous domain boundaries in the poly[bis(trifluoroethoxy) phosphazene coating (see FIG. 11B). Most of the microparticles showed only minor defects (such as a minor circular patch being missing), but no damage to the hull of the microparticles (see FIGS. 11C and 11D).

EXAMPLE 15

Microparticles were formed in accordance with a preferred embodiment herein. A deionized water solution of polyvinyl alcohol (PVA) was prepared using about 23 g of PVA of weight average molecular weight of about 85,000-124,000, which PVA was about 87-89% hydrolyzed and 1000 g water. A phosphate buffer solution was prepared using 900 g deionized water, 4.53 g disodium hydrogen phosphate, 0.26 g sodium dihydrogen phosphate and 0.056 g ethylenediamine tetraacetic acid (EDTA). Methyl methacrylate (MMA) monomer was vacuum distilled prior to use.

Polymerization was carried out in a three-necked, round-bottomed, 2000-ml flask with a KPG mechanical stirring apparatus attached. The flask was also equipped with a thermometer, reflux condenser and a pressure release valve with a nitrogen inlet. The polymerization process further utilized 100 ml of the PVA solution prepared above, 900 ml of the phosphate buffer solution, 0.65 g of dilauroyl peroxide, 200.2 g methacrylic acid methyl ester and 2.86 g triethylene glycol dimethacrylate.

The PVA and buffer solutions were provided to the reactor flask. The distilled MMA and triethylene glycol dimethacrylate were introduced, dilauroyl peroxide then added to the same flask and the components were agitated to ensure dissolved solids. The reaction flask was flushed with argon and the stirrer speed set to at 150 rpm to produce particle sizes of a majority in the range of 300-355 μm. Stirring continued for approximate 5 minutes. The stirrer was then set to 100 rpm and argon flushing was discontinued. The reaction flask was then subjected to a water bath which was heated to 70° C. and held at approximately that temperature for about 2 hours. The temperature of the bath was then increased to 73° C. and held for an hour, then the water bath temperature was raised again to 85° C. and held for another hour. The stirring and heat were discontinued. The solution was filtered and the resulting polymethylacrylate microparticles were dried in an oven at 70° C. for about 12 hours. The microparticles were subjected to sieving and collected in size fractions of from 100-150; 150-200; 200-250; 250-300; 300-355; 355-400; and 400-450 μm with a maximum yield at 300-355 μm.

The PMMA microparticles thus formed were then hydrolyzed. A portion of 100 g 250-300 μm sized microparticles, 150 g potassium hydroxide and 1400 g of ethylene glycol were added to a 2000 ml flask, reflux condenser with drying tube connected, and the mixture was heated at 165° C. for 8 hours for full hydrolysis. The mixture was allowed to cool to room temperature, solution decanted and the microparticles were washed with deionized water. The procedure was repeated for other calibrated sizes of microparticles (the following reaction times applied: 300-355 micron particles: 10 hours; 355-400 micron particles: 12 hours and 400-455 micron particles: 14 hours).

The microparticles were finally acidified with hydrochloric acid to a pH of 7.4, and dried in an oven at approximately 70° C.

EXAMPLE 16

Microparticles formed in accordance with Example 15 were then esterified in this Example. For esterification surface treatment, 800 g of dried microparticles from Example 15 were weighed in a 2 L reaction vessel with a reflux condenser. 250 g thionyl chloride in 1.5 L diethyl ether were added under stirring. Stirring was continued at room temperature for 20 hours. The solvent and volatile reactants were removed by filtration and subsequent vacuum drying. Then 500 g trifluoroethanol in 1.5 L ether were introduced and the suspension stirred for another 20 hours at room temperature. The particles were finally dried under vacuum.

EXAMPLE 17

In an alternative surface treatment to Example 16, 800 g dried microparticles from Example 15 were reacted with 1140 g trifluoroethanol and 44 g sulfuric acid added as a catalyst. The mixture was stirred for 20 hours at room temperature, filtered and dried under vacuum.

EXAMPLE 18

800 g of dry PMMA potassium salt microparticles which were partially esterified with trifluoroethanol as described above in Examples 15-16 were spray coated with poly[bis (trifluoroethoxy)phosphazene in an MP-1 Precision Coater™ fluidized bed coating apparatus (available from Aeromatic-Fielder AG, Bubendor, Switzerland). The particles were picked up by an air stream (40-60 m$^3$/h, 55° C. incoming temperature) and spray coated with poly[bis(trifluoroethoxy)phosphazene solution microdroplets from an air-fluid coaxial nozzle. The solution composition was 0.835 g poly[bis(trifluoroethoxy)phosphazene, 550 g ethyl acetate and 450 g isopentyl acetate. It was fed through the nozzle's 1.3 mm wide inner bore at a rate of 10-30 g/min. At the nozzle head, it was atomized with pressurized air (2.5 bar). The total amount of spray solution (3 kg) was calculated to coat the particle with a 150 nm thick poly[bis(trifluoroethoxy)phosphazene film.

EXAMPLE 19

The dry potassium salt microparticles of Examples 15-16, which were partially esterified with trifluoroethanol as described above, were spray-coated with diluted poly[bis (trifluoroethoxy) phosphazene solution in ethyl acetate in a commercially available fluidized bed coating device (see Example 16). 100 mg of such coated, dried microparticles as well as 100 mg of uncoated, dried PMA potassium salt microparticles which were partially esterified with trifluoroethanol, were immersed in about 30% aqueous cesium chloride solution, prepared by dissolving 30.0 g cesium chloride in 100 ml deionized water. The supernatant liquid was decanted after 10 min. equilibrium time and the microparticles were washed thoroughly with deionized water, equilibrated for another 10 min., decanted and suspended in 3 ml surfactant free phosphate buffer solution at a pH of 7.4. Density of the particles in solution was measured for matching density in a contrast agent solution. To each type of microparticle was added a contrast agent solution which included a ratio of 3.5 ml of Imeron® 300 contrast agent (density 1.335 g/ml) and 4 ml phosphate buffered saline (density 1.009 g/ml). Both hydrogel types reached buoyancy at levels of 45-50% contrast agent in solution. This corresponds to an increased density of the microparticles of 1.16 g/ml.

EXAMPLE 20

Microparticles were formed in accordance with the procedure of Example 15 with the exception that an exterior barium sulfate coating was prepared on the microparticles after neutralization of the particles and the microparticles were not dried after neutralization prior to the barium sulfate coating step. To prepare the barium sulfate coating, 2500 ml hydrated particles were subjected to 2000 ml of 0.5 M sodium sulfate ($Na_2SO_4$) solution and saturated for 4-12 hours. To the particle suspension was then slowly added 1950 ml of 0.5 M barium chloride ($BaCl_2$) solution under stirring at room temperature. After washing with excess deionized water, the resulting particles in a swollen state included a barium sulfate powder coated surface. The particles were then dried and esterified in the manner noted above in Example 16. The particles were then coated using the fluidized bed process of Example 21 below. The resulting microparticles were externally coated with a non-adhesive barium sulfate powder. Barium sulfate coatings prepared in accordance with this invention and procedure are capable of preventing particle agglomeration during drying and also increase density. The concentration and ratios of barium sulfate may be varied to provide different results and a use of an excess of sodium sulfate can minimize residual barium chloride. The particles formed in accordance with this example were effectively washed with hot water to minimize excess barium sulfate powder that may contaminate vials, etc. The barium sulfate works effectively to prevent adhesion of particles prior to drying to assist in fluidization of the hydrated microparticles.

EXAMPLE 21

Fluidized bed coating of barium sulfate powdered beads was performed using polymethacrylate beads with a surface layer of barium sulfate formed in accordance with Example 20 but an excess of barium chloride was used such that barium ions diffused inside the core and formed a precipitate inside the hydrogel core.

In preparing the particles, the same procedure for barium sulfate coated particles set forth in Example 20 was repeated with the exception that the order of addition was reversed. Thus, 2500 ml hydrated microparticles were suspended in 2500 ml deionized water and slowly, 5 mol % (200 ml) of a 0.5 M ($BaCl_2$) were added slowly under stirring. The addition was performed within a time period of three minutes to prevent irreversible barium acrylate formation taking place. The suspension was then immediately quenched with the double amount (400 ml) of 0.5 M sodium sulfate ($Na_2SO_4$) solution under stirring at room temperature. Afterwards, the particles were washed three times with 2 L of deionized water each. This procedure precipitated barium sulfate inside the particles.

The resulting precipitate was precipitated within the pores of the hydrogel core and could not be removed by multiple washings with water. The particles thus formed were found to have a permanent increased density in contrast to unmodified particles. The density increase was controllable by the molar amount of barium chloride used. Amounts ranging from 0-15 mol % of barium chloride were used reproducibly with this procedure. It was observed during evaluations of this procedure that, if the time period of addition exceeded 5 minutes, based upon the diffusion speed of barium chloride within the particles, the outer pores of the hydrogel core became irreversibly crosslinked, thereby preventing the barium sulfate precipitate inside from leaching out. This effect was visible by optical microscopy as the "diffusion front" of the barium sulfate was clearly visible as a white band inside the particle, whereas the surface remained clear.

Both Examples 20 and 21 provided particles having anti-adhesive properties that tend not to agglomerate during drying processes; therefore avoiding surface damage. Generally, such an advantage helps minimize the amount of particles needed for a fluidized bed procedure as the particles can be fluidized without being completely dried. The residual water content may be increased up to 1:1 based on dry weight without agglomeration. The Examples also produce particles with increased density properties wherein the density change appears to be permanent.

It should also be understood according to this disclosure that generally when applying the procedures noted herein, barium sulfate may be introduced in accordance with the invention in a range of from 0 to about 100 mol %, and preferably 0 to about 15 mol % to provide particles that have preferred elasticity, density and mechanical stability properties.

The particles formed according to this Example having a barium sulfate load inside the core were then esterified according to Example 16 and vacuum-dried. 300 g of the dry beads were suspended in 300 g water which was completely absorbed by the polymethacrylate cores within less than 1 min while the barium sulfate powdered particle surface appeared dry and the particles showed no tendency to agglomerate.

The particles (now 600 g) with 50 weight percent (wt %) water inside were spray coated with APTMS/poly[bis(trifluoroethoxy)phosphazene in an MP-1 Precision Coater™ fluidized bed coating apparatus according to Example 18 with the exception that an additional aminosilane adhesion promoter was used. The process equipment used was the same as that of Example 18, but the coating provided included three different layers. A bottom coating of 3-aminopropyltrimethoxysilane (APTMS) adhesion promoter was provided upon which was a second coating layer of a mixture of APTMS and poly[bis(trifluoroethoxy)phosphazene and a third, top coating layer of poly[bis(trifluoroethoxy)phosphazene. All three spray solutions were prepared by dissolving the coating material in isopentyl acetate and ethyl acetate in a 1:1 weight percentage ratio mixture. The first solution included 35 µl APTMS dissolved in 200 g acetate mixture. The second solution included 25 µl APTMS and 125 mg poly[bis(trifluoroethoxy)phosphazene in 150 mg of the acetate mixture and the third included 50 mg poly[bis(trifluoroethoxy)phosphazene in 60 g of the acetate mixture. The spray solution quantities and concentrations refer to the coating of a 300 g batch with 350 µm particles. The absorbed water evaporated at a rate of 5-10 g/min. The process was stopped after 30 min when the coating thickness reached 100 nm and the residual water content was 18.4 wt %.

EXAMPLE 22

The absorption of organic dyes was tested on microparticles formed according to Example 15. To 2 ml of phosphate buffered saline solution containing 1 ml of hydrated beads was provided an amount of 5-10 µl of the respective dye as a 10 millimolar solution in ethanol. The samples were incubated for 30-60 minutes at room temperature under gentle shaking of the vial. Supernatant liquid was discarded and particles were washed three times with 2 ml of either deionized water, saline or PBS buffer solution prior to visualization with optical and fluorescence microscopy. The dyes tested included triphenylmethane derived dyes such as Fluoescein diacetate and Rhodamin 6G which were evaluated along with carbocyanine based dyes such as DiI. The triphenylmethane based Fluorecein and Rhoamine dyes exhibited a specific affinity for the hydrophilic PMMA hydrogel core through ionic interactions. They were able to easily withstand the rigorous conditions of repeated washing and steam sterilization without substantial leaching.

The carbocyanine dye DiI on the other hand exhibited a high selectivity for the hydrophobic poly[bis(trifluoroethoxy) phosphazene shell, without penetrating the hydrophilic PMAA core material. Thus with the subsequent staining employing the combination of DiI and Fluorescein diacetate both core and shell could be simultaneously visualized employing a fluorescence optical microscope. As a result, this procedure provides a fast, sensitive fluorescence-staining assay for the PMAA particles that makes core and shell simultaneously visible under conditions encountered in actual application. This procedure further enables assessment of the mechanical-elastic stress or damage to the poly[bis(trifluoroethoxy)phosphazene shell. It further shows the affinity of certain classes of dyes for the various components of the particle.

Figure 12A:
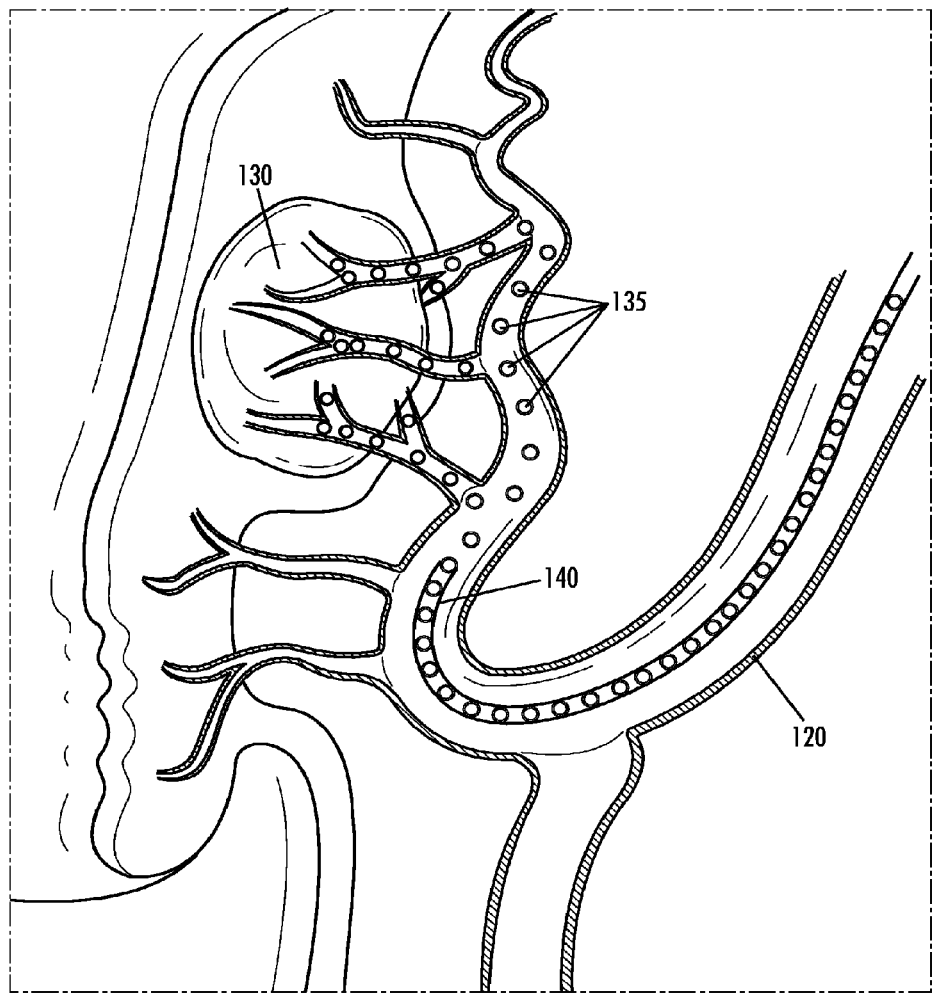
FIGS. 12A and 12B illustrate various aspects the microparticles formed and used according to Examples 22 and 23.

Use of these and other dyes may be used to visually identify selected microspheres, which may be provided and dyed for identification to indicate certain sizes of microspheres for use in selected clinical or diagnostic applications. Color-coding may also be used to identify selected microspheres on the basis of other properties, such as content of certain therapeutic or diagnostic agents. Applications according to the present invention may also improve the imaging visualization by enhancing the particles' buoyancy behavior FIG. 12A shows exemplary microspheres A, B, and C of the present invention, in which the microspheres are each of different diameters, and each has a different color-coding. In an exemplary use of such microspheres of the present invention, color-coded microspheres of like sizes may be separately packaged and supplied for use. Such color-coded microspheres may provide a user a visual indication of the specific microsphere in a particular clinical or diagnostic use.

In various embodiments according to the present invention, microspheres may be produced in calibrated sizes ranging from about 1 to about 10,000 nanometers in diameter. In one embodiment of the present invention, microspheres of the present invention may be provided in sizes of about 40, about 100, about 250, about 400, about 500, about 700, and about 900 nanometers in diameter, with a visually distinctive color imparted to each size of microsphere. Other sizes, size ranges, and calibrated sized microspheres lacking color dye are also included in the present invention. Not only may the microspheres or particles be provided in different size ranges, but their elasticity may be controlled according to the present invention to specifically provide for proximal or distal embolization behavior, due to potentially differing ranges of compressibility which may alter the traveling distance of the particles or microspheres upon their release within a selected blood vessel. Microspheres of the present invention may also be provided in customized sizes and/or with customized colors as specified by a user for specific clinical diagnostic or therapeutic applications.

EXAMPLE 23

Transarterial chemoembolization or TACE is a clinical procedure in which the blood supply to a tumor is disrupted by embolization and chemotherapy is administered directly into the tumor. Selective embolization of tumor blood vessels without direct administration of chemotherapy (bland embolization) is also preformed as a clinical procedure in certain situations.

In most living organisms with a developed circulatory system, the vasculature tends to taper from larger diameter vessels proximal to the heart to smaller vessels more distal to the heart. Larger arteries thus tend to divide into smaller arteries, which eventually taper to the arteriole level and interface with small diameter venules. Venous flow progresses from such venules through successively larger diameter veins as flow returns to the heart.

It is common, therefore, that blood vessels of differing sizes may exist within a tumor mass or other target tissue. In a clinical situation where embolization and maximal disruption of blood supply to a tumor or other target tissue is desired, serial embolization of progressively larger tumor vessels may provide a more complete embolization, with or without the delivery of chemotherapeutic or other therapeutic agents.

Figure 12B:
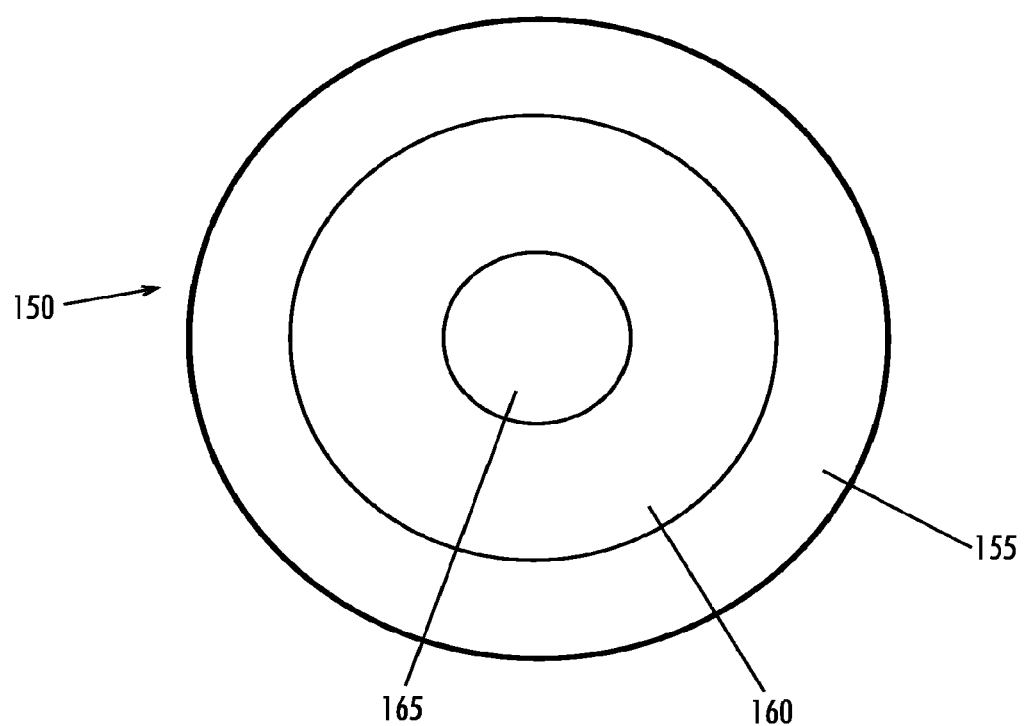

FIG. 12B is a conceptual representation of a selective embolization of an exemplary artery 120 by serial administration of different sized microspheres 121, 122, and 123. The direction of blood flow within the exemplary artery 120 is shown by the arrows in FIG. 12B. In this example, microsphere 121 is the smallest diameter of the microspheres administered, and is injected into artery 120 first, occluding the vessel lumen at the smallest vessel diameter that will not permit passage of microsphere 121. Continuing in this example, microsphere 122 is of intermediate diameter of the microspheres administered, and is injected into artery 120 first, occluding the vessel lumen at the smallest vessel diameter that will not permit passage of microsphere 122. Finally, in this example, microsphere 123 is the largest diameter of the microspheres administered, and is injected into artery 120 first, occluding the vessel lumen at the smallest vessel diameter that will not permit passage of microsphere 123. The result in this example is the sequential blockage of blood flow at multiple levels throughout the blood supply of the tumor or target tissue.

In other examples of the present invention, less than three or more than three different sized microspheres may be administered to secure the desired embolization of a tumor or other target tissue.

As provided in previous examples of the present invention, different-sized microspheres of the present invention may further be provided with color-coding to allow user identification and visual confirmation of the sized microspheres in use at any given stage of the clinical procedure.

The delivery of microspheres of different sizes or other inherent qualities may further be facilitated by the use of transport packaging and/or delivery devices which are color-coded to allow user identification and visual confirmation of the sized microspheres in use at any given stage of the clinical procedure in exemplary applications according to the present invention. In various exemplary applications of the present invention, such color-coded devices may be used in combination with color-coding of the microspheres themselves, with corresponding microsphere and packaging/delivery device color-coding.

FIG. 12C shows a syringe used for the packaging and/or delivery of color-coded microspheres of a select size according to the present invention. In the example shown in FIG. 12C, the syringe 124 comprises a barrel 125, a plunger 126, a plunger tip 127, a Luhr-type injection tip 128, and a Luhr tip cover 129.

As shown in FIG. 12C, one or more of components barrel 125, a plunger 126, a plunger tip 127, a Luhr-type injection tip 128, and a Luhr tip cover 129 may be colored in a common color according to a color code to indicate a desired property of the microspheres contained therein. In one example of the present invention, a syringe may contain color-coded microspheres to indicate a certain microsphere size, and the syringe plunger, plunger tip, and Luhr tip cover may be similarly colored to further indicate the desired property of the contained microspheres to a user.

FIG. 12D is a conceptual representation of a selective embolization of an exemplary tumor mass 130 by intravascular administration of microspheres 135. The direction of blood flow within the exemplary artery 120 is shown by the arrows in FIG. 12. In this example, microspheres 135 are injected into artery 120 through a catheter 140. The result in this example is the sequential blockage of blood flow throughout the blood supply of the tumor.

FIG. 12E shows an exemplary particle of the present invention comprising a microsphere 150 with a polyphosphazene coating 155, further comprising a core 160 with a gas-filled microbubble 165 for enhanced visibility of sonography. Particles of this type may be used by administering to an ultrasound subject at least one particle comprising poly[bis(trifluoroethoxy)phosphazene] and/or a derivative thereof and a core containing one or more gas filled microbubbles to an area of the ultrasound subject to enhance echogenicity therein, and imaging the area of the subject using ultrasound.

EXAMPLE 24

In conventional radiology, including fluoroscopy, tomography and computerized axial tomography (CT) imaging modalities, it is often useful to employ contrast agents to identify certain sites in a mammalian body that would otherwise be difficult to distinguish from adjacent body tissues. This is particularly applicable in the evaluation of tissue that has been embolized, such as a solid tumor mass.

Selective embolization of a solid tumor mass with microspheres of the present invention comprising a coating of poly[bis(trifluoroethoxy) phosphazene] surrounding a core containing a contrast agent such as barium sulfate or iodine will permit the visualization of the embolized microspheres on plain x-ray or CT scanning. Serial examinations may show changes in tumor size following embolization therapy.

EXAMPLE 25

As an alternative embodiment to having a contrast agent within the structure of microspheres of the present invention, selective embolization of a solid tumor mass with microspheres of the present invention comprising a coating of poly[bis(trifluoroethoxy)phosphazene may be achieved using a contrast agent in solution, such as an iodine-containing solution, as a suspension/delivery solution for injection delivery of the microspheres through a catheter, needle, or cannula placed into arterial blood vessels feeding the targeted tumor mass. The presence of the contrast agent will allow visualization of the tumor mass immediately before and after its embolization.

EXAMPLE 26

Selective embolization of a solid tumor mass with microspheres of the present invention comprising a coating of poly[bis(trifluoroethoxy)phosphazene surrounding a core containing a radioisotope as a tracing agent will permit the visualization of the embolized microspheres on scintillation studies. Depending upon the half-life of the radioisotope selected, residual radiation may be detected in the site for some time, allowing serial examinations which may show changes in tumor size following embolization therapy.

EXAMPLE 27

Magnetic Resonance Imaging (MRI) may be used to assess and follow tumor size following selective embolization of a solid tumor mass with exemplary microspheres of the present invention comprising a coating of poly[bis (trifluoroethoxy)phosphazene surrounding a core containing a contrast agent such as tantalum, gadolinium and samarium-chelates, or other rare earth compounds with paramagnetic properties. The response of such a contrast agent to the strong electrical field of the MRI process provides enhanced imaging results in the targeted, embolized tumor tissue.

EXAMPLE 29

At the onset of an interventional embolization procedure, a patient containing a targeted tissue is injected by an operator with exemplary first microspheres of the present invention comprising a coating of poly[bis(trifluoroethoxy) phosphazene surrounding a core containing a contrast agent. The exemplary microspheres are selected of a relatively smaller size range, suited for the given medical indication for the procedure.

The smaller-sized first microspheres in this example may be marked with one or more specific contrast agents covalently bound to the hydrogel core. Such contrast agents are selected depending upon the imaging technology in use. For magnetic resonance imaging (MRI), ionic or non-ionic contrast agents including, but not limited to tantalum, gadolinium and samarium-chelates, or other rare earth compounds with paramagnetic properties, or MRI active ions, such as Mn or Fe ions.

Once selectively injected under real-time MRI or other imaging visualization, these specifically marked first microspheres will travel far more distally in the injected vascular system due to their smaller size.

The interventional procedure is then continued with the administration of second, larger microspheres of the present invention under real time imaging control, until the operator identifies the retardation of blood flow and beginning of vascular saturation in the targeted tissue. These larger second microspheres travel more proximally (relative to the administrator of the microspheres, not the targeted tissue) in the injected vascular system than the first microspheres previously injected.

To conclude the embolization procedure, the operator may inject differently marked third microspheres of the present invention of larger sizes. These specifically marked third microspheres will travel more proximally in the injected vascular system than the first or second microspheres previously injected.

The contrast agent(s) within the first, second, or third microspheres of this example may be of different or the same chemical nature, thereby making it possible to distinguish the first, second, and third microspheres in situ in real time using MRI or other imaging modalities during the interventional procedure.

The operator may thereby determine the start and endpoints of the embolization procedure, as well as the specific anatomic location of the vascular region embolized, and may further determine the distance between most proximal and distal embolization regions and the effect of different size microspheres in the embolized vascular regions.

The exemplary materials and techniques disclosed herein are applicable to all size ranges of microspheres of the present invention and to all clinical embolization fields. The resulting embolization procedures offer superior benefit with increased safety and effectiveness to intracranial, intrathoracic, intraabdominal, retroperitoneal, and other embolization procedures. These procedures as described may also provide valuable opportunities for radiological research.

In alternate embodiments an operator may inject mixtures of sized embolic microspheres of the present invention, with each size distinctly marked with an appropriate contrast agent, Such mixtures of differing sized microspheres may be allowed to settle at random, aiding the operator in determining the best size range for a needed embolization and better revealing the local vascular distribution of different contrast agents.

MRI contrast agents in exemplary embodiments of the present invention include products such as Magnevist, Prohance, and Omniscan. These agents are generally nonionic and a recent report, points out that the development of nonionic contrast agents for MRI has paralleled that for iodinated contrast materials. Ionic chelates are also hyperosmolar and some of their side effects may be attributed to this property. Gadodiamide (Omniscan, Winthrop Pharm.) is a nonionic complex with two-fifths of the osmolality of Gd-DTPA. It has a median lethal dose of 34 mmol/kg resulting in a safety ratio of 2-3 times that of Gd-DOTA, and 3-4 times that of Gd-DTPA. No abnormal serum bilirubin levels occur, however elevated serum iron levels occurred with an incidence of 8.2% in one study of 73 patients. The efficacy of this contrast is similar to that of Gd-DTPA. Gadoteridol (Prohance, Squibb) is the third intravenous contrast agent on the market. It is a low osmolar, nonionic contrast as is Gadodiamide. Indications for use and efficacy are similar to the other agents.

Alternately, contrast agents such as Ultrasmall Supermagnetic Iron Oxide Particles or small particles of ferrite or other metallic compounds or particles comprising Mn, may be used as paramagnetic contrast agents for MR imaging according to the present invention. These contrast agents exhibit strong T1 relaxation properties, and due to susceptibility differences to their surroundings also produce a strongly varying local magnetic field, which enhances T2 relaxation to darken the contrast media-containing structures. As particulate matter they are taken up by the RES. Very small particles of less than 300 nanometers also remain intravascular for a prolonged period of time and thus can serve as blood pool agents. The agents are also known by the abbreviation SPIOs ("small particle iron oxides" or "superparamagnetic iron oxides") and USPIOs ("ultrasmall particle iron oxides" or "ultrasmall superparamagnetic iron oxides").

The contrast agents within the hydrogel cores of microspheres of the present invention may be chosen depending upon the imaging modality available and appropriate for the clinical application. Such imaging modalities include, but are not limited to, fluoroscopy, computerized tomography, tomography, scintillation camera, ultrasound, computerized ultrasound, or positive emission tomography. Contrast agents may be selected that provide best visualization with the intended imaging technology, and these agents may them be covalently bonded to the hydrogel cores of the microspheres as described herein.

It will be appreciated by those possessing ordinary skill in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method of performing a selective embolization, the method comprising:
   a) selecting a targeted tissue within a mammalian patient; and
   b) delivering to the targeted tissue one or more first particles, the first particles each comprising a core and a coating;
   wherein the first particle core comprises a first acrylic-based hydrogel polymer; and
   the first particle coating comprises a poly[bis(trifluoroethoxy)phosphazene] and/or a derivative thereof.

2. The method of claim 1, wherein the acrylic-based hydrogel polymer comprises a polymethyl methacrylate hydrolyzed with potassium hydroxide.

3. The method of claim 1, wherein the poly[bis(trifluoroethoxy)phosphazene] is poly[bis(2,2,2-trifluoroethoxy)]phosphazene or a derivative of poly[bis(2,2,2-trifluoroethoxy)]-phosphazene.

4. The method of claim 1, wherein the first particle core comprises a contrast agent.

5. The method of claim 4, wherein the contrast agent is selected from Diatrizoate, Metrizoate, Ioxaglate, Iopamidol, Iohexyl, Ioxilan, Iopromide, Iodixanol, Ioxitalamin, or a combination thereof.

6. The method of claim 4, wherein the contrast agent is selected from $^{67}$Ga, $^{68}$Ga, $^{123}$I, $^{126}$I, $^{131}$I, $^{132}$I, $^{133}$I, $^{111}$In, $^{113}$In, $^{201}$Tl, $^{203}$Tl, $^{3}$H, $^{11}$C, $^{14}$C, $^{13}$N, $^{18}$F, $^{22}$Na, $^{24}$Na, $^{31}$Si, $^{32}$P, $^{35}$S, $^{36}$Cl, $^{38}$Cl, $^{42}$K, $^{45}$Ca, $^{51}$Cr, $^{52}$Mn, $^{54}$Mn, $^{55}$Fe, $^{59}$Fe, $^{60}$Co, $^{63}$Zn, $^{65}$Zn, $^{86}$Zn, $^{82}$Br, $^{85}$K, $^{85}$Kr, $^{89}$Sr, $^{99}$Tc, $^{99m}$Tc, $^{99m}$Re, $^{105}$Re, $^{105}$Re, $^{121m}$Te, $^{122m}$Te, $^{125m}$Re, $^{137}$Cs, $^{165}$Tm, $^{167}$Tm, $^{168}$Tm, $^{81m}$Kr, $^{33}$Xe, $^{90}$Y, $^{3}$Bi, $^{77}$Br, $^{18}$F, $^{95}$Ru, $^{97}$Ru, $^{103}$Ru, $^{105}$Ru, $^{107}$Hg, $^{203}$Hg, $^{182}$Ta, $^{192}$Ir, $^{198}$Au, or a combination thereof.

7. The method of claim 4, wherein the contrast agent is selected from a tantalum compound, a gadolinium compound, a samarium-compound, a paramagnetic rare earth compound, ferric chloride, ferric ammonium citrate, gadolinium-DTPA, gadolinium-DOTA, gadolinium-EDTA, GdCl$_3$, Gadodiamide, Gadoteridol, gadopentetate diglumine, a Cr(III) compound, a manganese compound, Mn(III) TPPS4 (manganese(III) tetra-[4-sulfanatophenyl]porphyrin), Fe(III)TPPS4 (iron(III) tetra-[4-sulfanatophenyl]porphyrin), manganese dichloride, iron(III) ethylenebis-(2-hydroxyphenylglycine), 99mTc-iminodiacetate, chromium diethyl HIDA meglumine, gadobenate dimeglumine, manganese(II)-dipyridoxal diphosphate, gadolinium oxide, a superparamagnetic iron oxide, a small particle iron oxide, an ultrasmall supermagnetic particle iron oxide, or an ultrasmall particle iron oxide.

8. The method of claim 1, further comprising:
   c) confirming delivery of the first particles to the targeted tissue using a suitable imaging technology.

9. The method of claim 8, further comprising:
   d) delivering to the targeted tissue one or more second particles, the second particles being larger than the first particles, each second particle comprising a core and a coating,
   wherein the second particle core comprises a second acrylic-based hydrogel polymer; and
   the second particle coating comprises poly[bis(trifluoroethoxy)phosphazene] and/or a derivative thereof;
   wherein the second acrylic-based hydrogel polymer is the same as or different from the first acrylic-based hydrogel polymer, and the second particles travel more proximally in the targeted tissue than the first particles.

10. The method of claim 9, wherein the second particle core further comprises a second contrast agent wherein the second contrast agent is the same or different from the first contrast agent.

11. The method of claim 9, further comprising:
    e) identifying the retardation of blood flow and the beginning of vascular saturation in the targeted tissue.

12. The method of claim 9, further comprising:
    f) delivering to the targeted tissue one or more third particles, the third particles being larger than the first and second particles, each third particle comprising a core and a coating,
    wherein the third particle core comprises a third acrylic-based hydrogel polymer; and
    wherein the third particle coating comprises poly[bis(trifluoroethoxy)phosphazene] and/or a derivative thereof;
    wherein the third acrylic-based hydrogel polymer is the same as or different from the first and second acrylic-based hydrogel polymer, and the third particles travel more proximally in the targeted tissue than the first or second particles.

13. The method of claim 12, wherein the third particle core further comprises a third contrast agent wherein the third contrast agent is the same or different from the first and/or second contrast agent.

14. The method of claim 12, further comprising:
    g) identifying an endpoint of a desired devascularization in the targeted tissue.

15. The method of claim 12, further comprising:
    g) determining the distance between proximal and distal embolization regions in the targeted tissue; and
    h) assessing the effect of the different particles in the embolization regions in the targeted tissue.

16. The method of claim 1, wherein the particles are delivered to the targeted tissue through blood vessels.

17. The method of claim 1, wherein delivery of the first particle to the targeted tissue results in devascularization of the targeted tissue.

* * * * *